(12) United States Patent
Miyama

(10) Patent No.: US 9,204,861 B2
(45) Date of Patent: Dec. 8, 2015

(54) ULTRASOUND DIAGNOSTIC APPARATUS AND METHOD OF DETERMINING A TIME INTENSITY CURVE

(71) Applicant: GE MEDICAL SYSTEMS GLOBAL TECHNOLOGY COMPANY, LLC, Waukesha, WI (US)

(72) Inventor: Koji Miyama, Tokyo (JP)

(73) Assignee: General Electric Company, Schenectady, NY (US)

( * ) Notice: Subject to any disclaimer, the term of this patent is extended or adjusted under 35 U.S.C. 154(b) by 429 days.

(21) Appl. No.: 13/661,719

(22) Filed: Oct. 26, 2012

(65) Prior Publication Data

US 2013/0116565 A1 May 9, 2013

(30) Foreign Application Priority Data

Oct. 28, 2011 (JP) ................. 2011-237869

(51) Int. Cl.
*A61B 8/00* (2006.01)
*A61B 8/08* (2006.01)

(52) U.S. Cl.
CPC ............... *A61B 8/481* (2013.01); *A61B 8/5276* (2013.01); *A61B 8/5223* (2013.01)

(58) Field of Classification Search
CPC .......... A61B 8/14; A61B 8/461; A61B 8/483; A61B 19/52; A61B 8/06; A61B 8/13; A61B 8/463; G03B 42/06
USPC ......................................... 600/407, 437, 443
See application file for complete search history.

(56) References Cited

U.S. PATENT DOCUMENTS

| | | | |
|---|---|---|---|
| 6,673,019 B2 * | 1/2004 | Kamiyama | 600/443 |
| 7,583,828 B2 * | 9/2009 | Hall et al. | 382/128 |
| 7,949,160 B2 | 5/2011 | Hashimoto et al. | |
| 8,096,950 B2 | 1/2012 | Tanigawa et al. | |
| 2010/0081938 A1 * | 4/2010 | Kato | 600/458 |
| 2011/0054314 A1 | 3/2011 | Tanigawa et al. | |
| 2012/0108970 A1 | 5/2012 | Miyama et al. | |
| 2012/0108971 A1 | 5/2012 | Miyama et al. | |

FOREIGN PATENT DOCUMENTS

| | | |
|---|---|---|
| JP | 2008196537 A | 8/1996 |
| JP | 2006110360 A | 4/2006 |
| JP | 2010075586 | 4/2010 |
| JP | 2011115457 A | 6/2011 |

* cited by examiner

Primary Examiner — Joel Lamprecht

(57) ABSTRACT

An ultrasound diagnostic apparatus is provided. The ultrasound diagnostic apparatus includes an image data generation unit configured to generate image data corresponding to one frame of a subject, based on sound ray data acquired by transmitting ultrasound to the subject, a high intensity image determination unit configured to compare strength of sound ray data corresponding to the one frame with a predetermined value and determine whether the one frame is a high intensity image, a setting unit configured to set a region of interest onto an image based on the image data generated by the image data generation unit, and a time intensity curve arithmetic unit configured to eliminate sound ray data corresponding to the region of interest in the high intensity image and perform an arithmetic operation on a time intensity curve in which pixel values of the region of interest set by the setting unit are made consecutive.

20 Claims, 16 Drawing Sheets

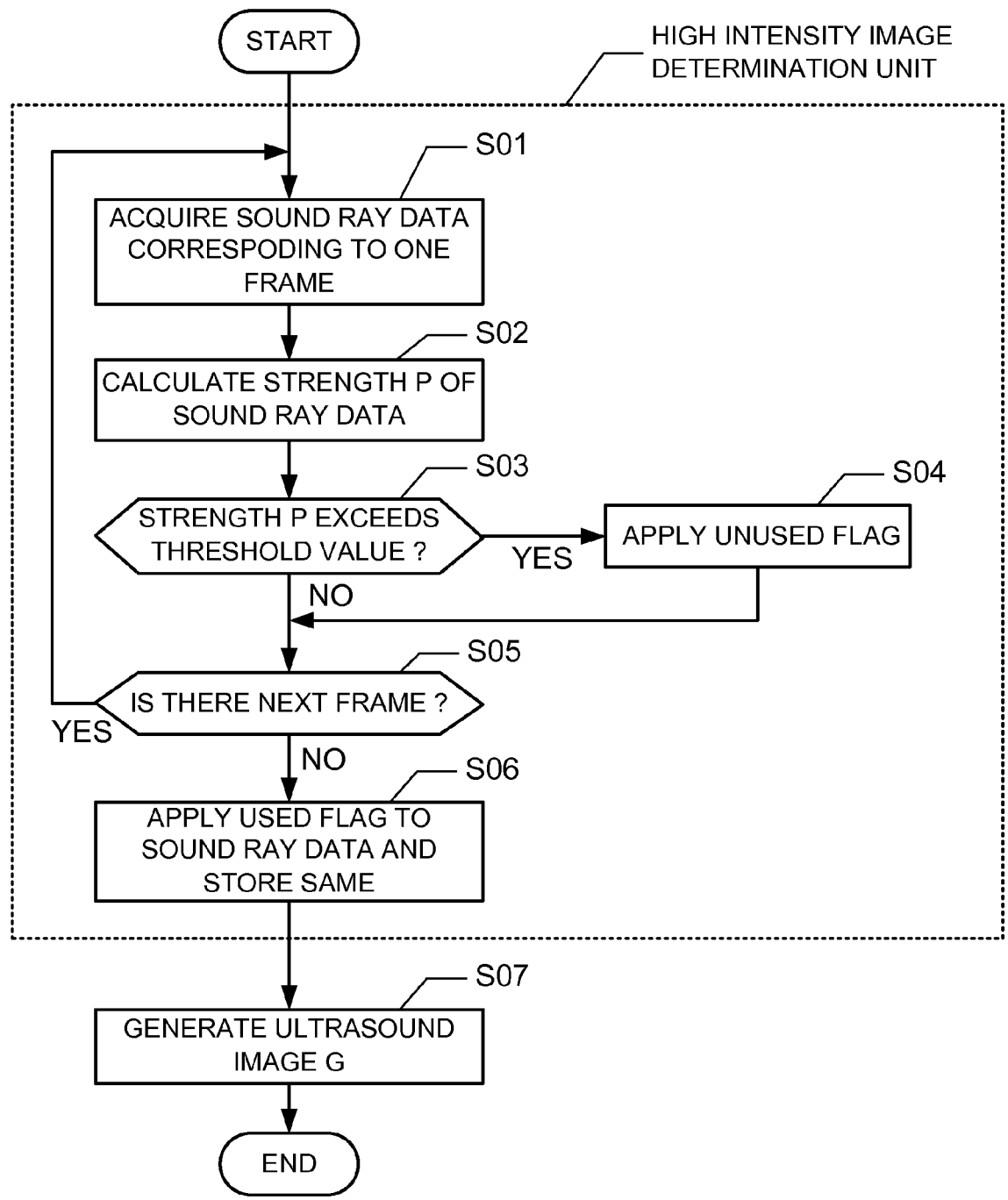

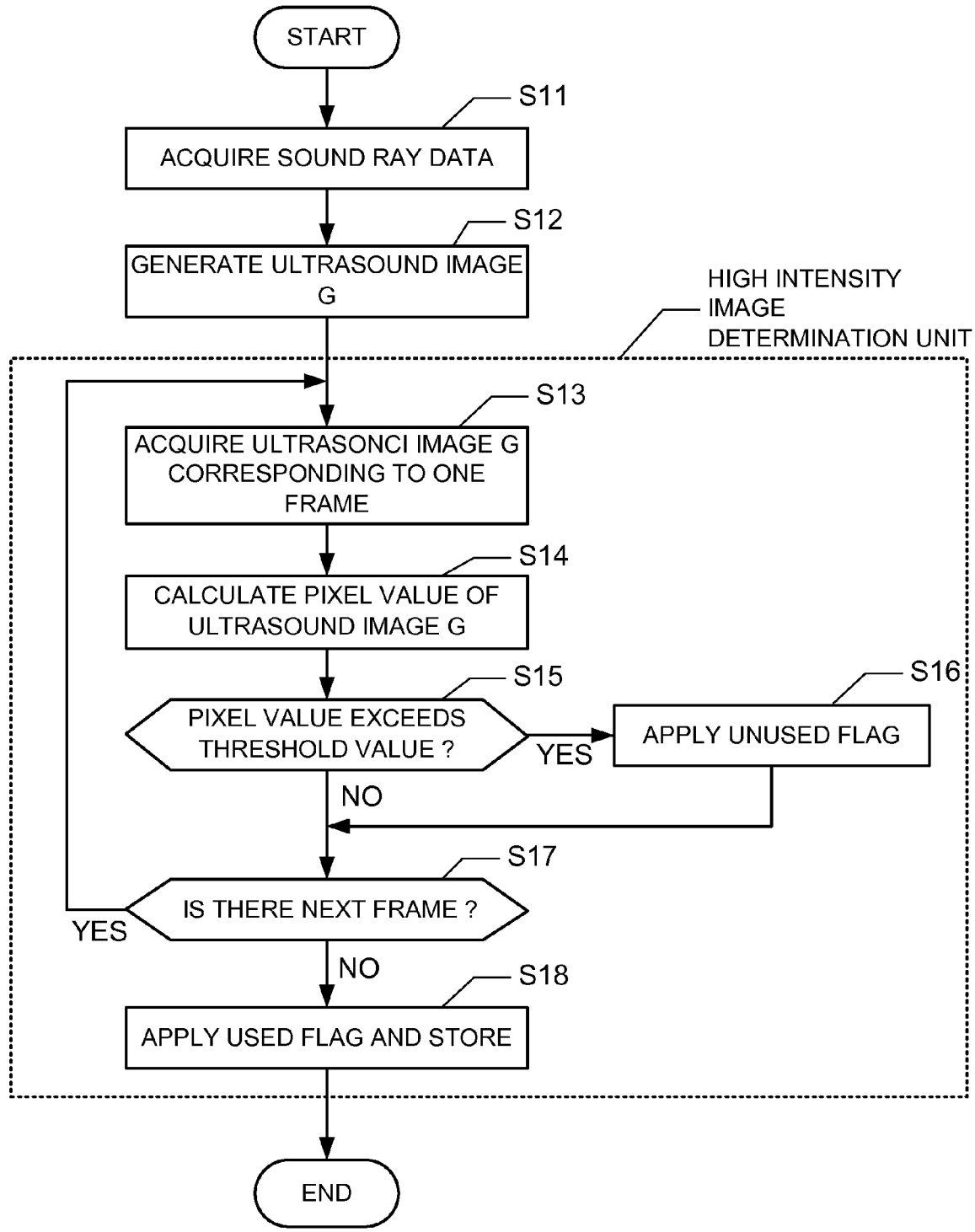

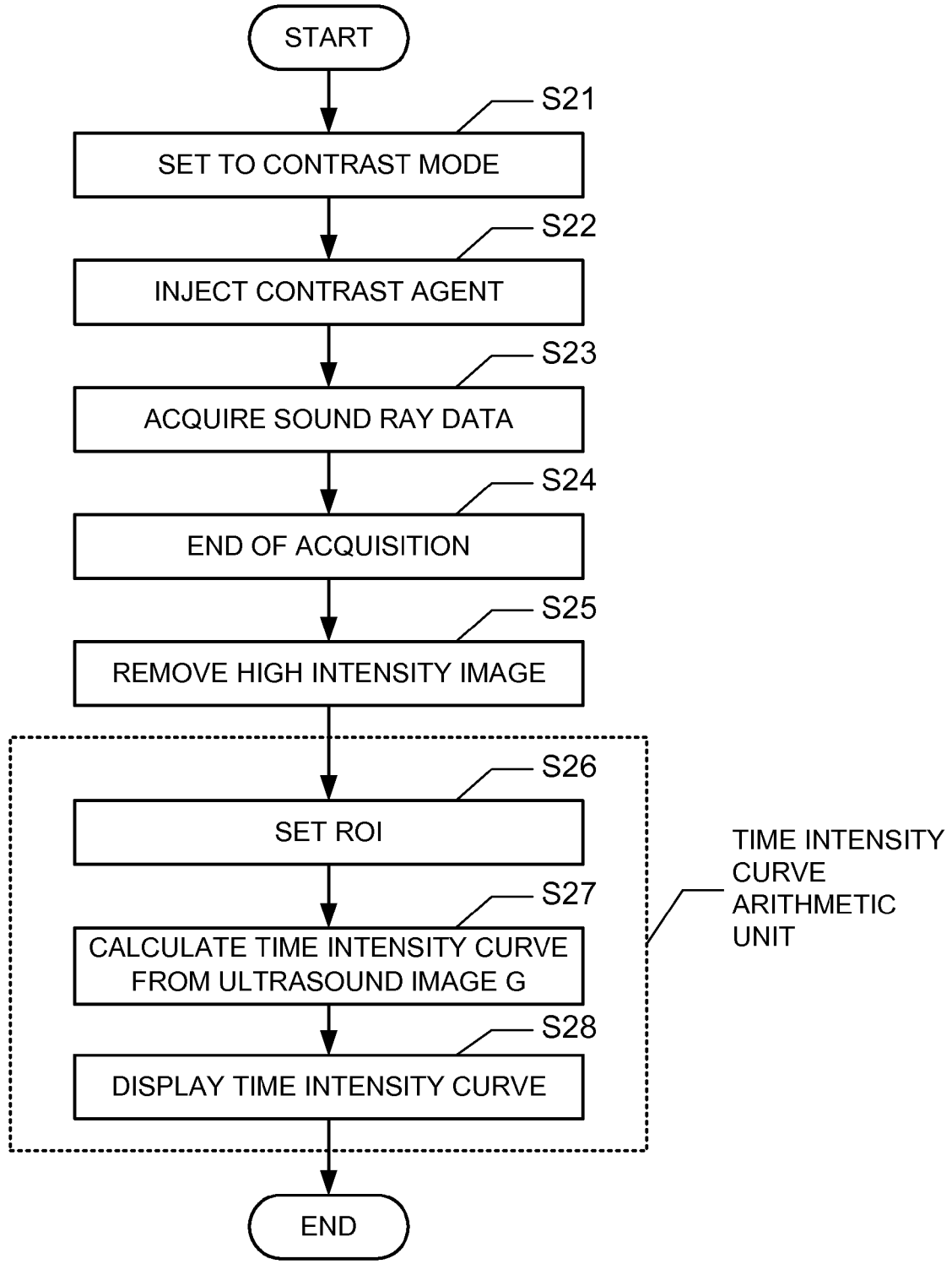

ULTRASOUND DIAGNOSTIC APPARATUS AND METHOD OF DETERMINING A TIME INTENSITY CURVE

CROSS REFERENCE TO RELATED APPLICATIONS

This application claims the benefit of Japanese Patent Application No. 2011-237869 filed Oct. 28, 2011, which is hereby incorporated by reference in its entirety.

BACKGROUND OF THE INVENTION

The present invention relates to an ultrasound diagnostic apparatus which determines a time intensity curve about a region of interest set to an ultrasound image.

A contrast agent may be injected into a body of a subject using, for example, an ultrasound diagnostic apparatus to perform imaging. Upon inspection using such a contrast agent, an inspection using a time intensity curve (TIC) may be carried out. The time intensity curve indicates a time change in the average pixel value in a region of interest (ROI) set onto an ultrasound image. Displaying the time intensity curve makes it possible to observe a change in the concentration of the contrast agent and diagnose the presence or absence of a disease in the subject or the degree thereof. There has been proposed in Japanese Unexamined Patent Publication No. 2010-075586 an invention in which when blood vessels are also included in a ROI in addition to a region target for observation of a time intensity curve, only a contrast agent penetrated into the region is observed using the time intensity curve except for a contrast agent that flows into the blood vessels.

In the related art, however, an artifact (virtual image) may exist in each ultrasound image acquired with time. As one example of the artifact, there is known a high intensity image. The high intensity image is generated from the motion of the subject or the motion of the heart close to the liver. Some or all of an area for the ultrasound image are brought to a high intensity. A problem arises in that a time intensity curve generated from a series of acquired images including such a high intensity image represents a false result according to a method of performing curve smoothing processing. Although a time intensity curve may be generated after a high intensity image has manually been eliminated in the related art ultrasound diagnostic apparatus, a problem arises in that it takes time for an operator to do the work of finding out a high intensity image and removing it.

It is desirable that the problems described previously are solved.

BRIEF DESCRIPTION OF THE INVENTION

In a first aspect, an ultrasound diagnostic apparatus is provided. The ultrasound diagnostic apparatus includes an image data generation unit which generates image data corresponding to one frame of a tomographic plane of a subject, based on sound ray data acquired by transmitting ultrasound to the subject to which an ultrasound contrast agent is administrated, a high intensity image determination unit which compares a strength of sound ray data corresponding to the one frame with a predetermined value and thereby determines whether the one frame is a high intensity image, a setting unit which sets a region of interest onto an image based on the image data generated by the image data generation unit, and a time intensity curve arithmetic unit which eliminates sound ray data corresponding to the region of interest in the high intensity image determined by the high intensity image determination unit and performs an arithmetic operation on a time intensity curve in which pixel values of the region of interest set by the setting unit are made consecutive.

In a second aspect, the ultrasound diagnostic apparatus described in the first aspect eliminates the sound ray data corresponding to the one frame determined to be of the high intensity image and performs an interpolation operation on the pixel value of the eliminated sound ray data, based on a pixel value of a frame prior to or subsequent to the one frame.

In a third aspect, an ultrasound diagnostic apparatus is provided. The ultrasound diagnostic apparatus includes an image data generation unit which generates image data corresponding to one frame of a tomographic plane of a subject, based on sound ray data acquired by transmitting ultrasound to the subject to which an ultrasound contrast agent is administrated, a high intensity image determination unit which compares a pixel value of the image data with a predetermined value and thereby determines whether the one frame is a high intensity image, a setting unit which sets a region of interest onto an image based on the image data generated by the image data generation unit, and a time intensity curve arithmetic unit which eliminates image data of the region of interest in the high intensity image determined by the high intensity image determination unit and performs an arithmetic operation on a time intensity curve in which pixel values of the region of interest set by the setting unit are made consecutive.

In a fourth aspect, in the ultrasound diagnostic apparatus described in the third aspect, when the average of the pixel values is greater than or equal to the predetermined value within the image data corresponding to the one frame at a screen corresponding to one frame, the high intensity image determination unit determines the image of the one frame to be a high intensity image.

In a fifth aspect, the ultrasound diagnostic apparatus described in the fourth aspect segments the image data corresponding to the one frame into a plurality of areas, and determines the image corresponding to the one frame to be a high intensity image when of the segmented areas, the areas in each of which the pixel value is greater than or equal to the predetermined value exist in plural form.

In a sixth aspect, in the ultrasound diagnostic apparatus described in the fifth aspect, when the pixel value is greater than or equal to the predetermined value in a plurality of areas including the region of interest, the image corresponding to the one frame is determined to be a high intensity image.

In a seventh aspect, a high intensity image decision is made which in the ultrasound diagnostic apparatus described in the third aspect, when the pixel value of each of image data corresponding to a sequence of plural frames is greater than or equal to the predetermined value, assumes each of images corresponding to the frames to be a high intensity image.

In an eighth aspect, a predetermined value of an ultrasound diagnostic apparatus is calculated from the entire average pixel value corresponding to a sequence of few frames in the ultrasound diagnostic apparatus described in the seventh aspect.

In a ninth aspect, a time intensity curve arithmetic unit is provided which in the ultrasound diagnostic apparatus described in each of the third through eighth aspects, eliminates image data corresponding to one frame determined to be the high intensity image and performs an interpolation operation on the pixel value of the eliminated image data, based on the pixel value of the frame prior to or subsequent to the one frame.

In a tenth aspect, in the ultrasound diagnostic apparatus described in each of the first through ninth aspects, the time intensity curve arithmetic unit performs an arithmetic operation on the average pixel value of the region of interest or the maximum pixel value thereof.

According to an ultrasound diagnostic apparatus of the described herein, pixel values of a region of interest in a high intensity image of consecutively acquired ultrasound images are automatically eliminated so that an accurate time intensity curve in the region of interest can be obtained.

Advantages of the embodiments describe herein will be apparent from the following description of the exemplary embodiments as illustrated in the accompanying drawings.

BRIEF DESCRIPTION OF THE DRAWINGS

FIG. 4 is a flowchart of a high intensity image determination unit which relates to sound ray data.

FIG. 5 is a flowchart of the high intensity image determination unit which relates to an ultrasound image G.

FIG. 6 is a flowchart of a series of contrast ultrasound inspections and a time intensity curve arithmetic unit.

DETAILED DESCRIPTION OF THE INVENTION

Exemplary embodiments will hereinafter be described in detail based on the accompanying drawings.

First Embodiment

Figure 1:
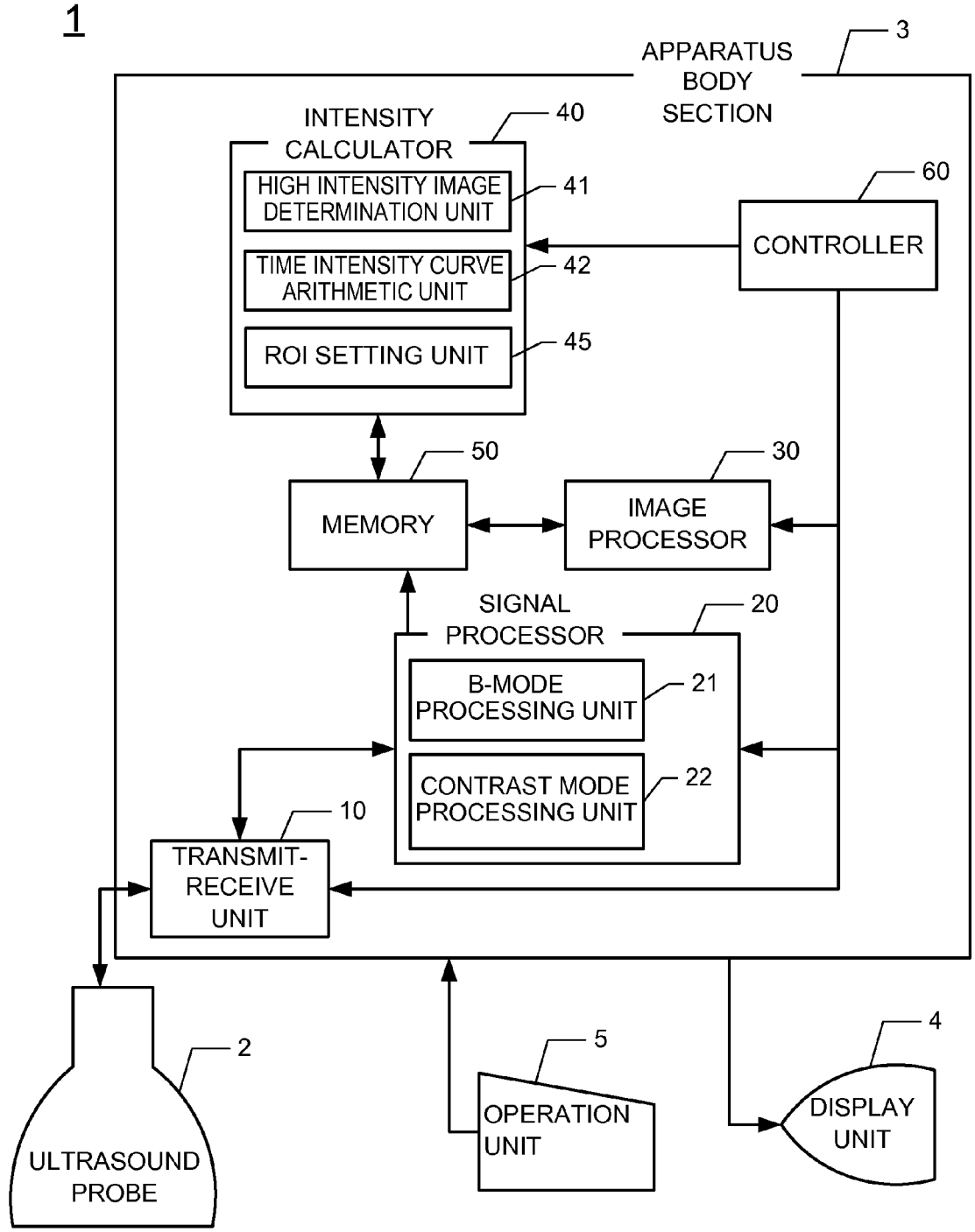
FIG. 1 is a block configuration of an exemplary ultrasound diagnostic apparatus.

FIG. 1 is a block configuration of an exemplary ultrasound diagnostic apparatus 1. The ultrasound diagnostic apparatus 1 includes an ultrasound probe 2, an apparatus body section 3, a display unit 4 and an operation unit 5.

The transmit-receive unit 10 drives the ultrasound probe 2 in accordance with respective modes of the signal processor 20 to transmit and receive ultrasound to and from the subject. The transmit-receive unit 10 delays the piezoelectric transducer of the ultrasound probe 2 for a predetermined time so that a desired transmission/reception beam is formed. Also the transmit-receive unit 10 performs digital conversion or analog conversion on transmission and reception signals. The received signal is stored as sound ray data in an image memory of the memory 50 to be described later. The transmit-receive unit 10 changes a scan method according to the ultrasound probe 2. The scan method may include a sector scan, a linear scan and a convex scan according to the ultrasound probe 2.

The transmit-receive unit 10 drives the ultrasound probe 2 in accordance with respective modes of the signal processor 20 to transmit and receive ultrasound to and from the subject. The transmit-receive unit 10 delays the piezoelectric transducer of the ultrasound probe 2 for a predetermined time so that a desired transmission/reception beam is formed. Also the transmit-receive unit 10 performs digital conversion or analog conversion on transmission and reception signals. The received signal is stored as sound ray data in an image memory of the memory 50 to be described later. The transmit-receive unit 10 changes a scan method according to the ultrasound probe 2. As the scan method, may be mentioned a sector scan, a linear scan and a convex scan according to the ultrasound probe 2.

The signal processor 20 performs signal processing that complies with various image display modes, based on each echo signal from the subject. The signal processor 20 includes a B-mode processing unit 21 or a contrast mode processing unit 22, which is selected according to the purposes of ultrasound diagnosis.

The B-mode processing unit 21 performs processing such as amplification, logarithmic compression, envelop detection or the like on the echo signal from the transmit-receive unit 10 to generate B-mode data (Brightness Mode Data). An ultrasound image G generated from the B-mode data is called a basic wave image (tissue image). The form of a target tissue can be observed with time at predetermined sampling intervals (i.e., a frame rate expressed in fps (frames per second)).

An ultrasound inspection (hereinafter called contract echo) in the contrast mode processing unit 22 is used where an ultrasound contrast agent containing microbubbles is injected in the body of the subject by intravenous injection. The ultrasound contrast agent has two features. One resides in that it collapses when subjected to ultrasound irradiation due to being the microbubbles. Another resides in that it exhibits a non-linear effect that is strong as compared to a biological body.

The contrast mode processing unit 22 makes use of the strong non-linear effect of the ultrasound contrast agent. In the non-linear effect, the wave reflected by each microbubble is distorted larger than an incident wave. The distortion of a waveform yields the generation of harmonic components. The contrast mode processing unit 22 makes use of this feature and particularly mainly uses a (Contrast Harmonic Imaging) method for suppressing a basic wave by bringing a Second Harmonic equivalent to twice the radiation wave into imaging and thereby emphasizing a contrast agent more. That is, in the Contrast Harmonic Imaging method, an image in which a wave reflected from the contrast agent has been emphasized is obtained since the wave reflected from each bubble includes a lot of second harmonics as compared to a wave reflected from a biological tissue. As the Contrast Harmonic Imaging method as well, there is known a filter method in which a filter is used as means for extracting a second harmonic wave, or a non-filter method free of the use of a filter. Since the second harmonic wave is extracted without using the filter, the non-filter method enables broad-band transmission/reception as compared with the filter method and enhances resolution and sensitivity. Observations are enabled with time at a predetermined frame rate even at the contrast echo.

The image processor 30 generates ultrasound images G corresponding to various image display modes, using the sound ray data stored in the memory 50.

The intensity calculator 40 includes a high intensity image determination unit 41, a time intensity curve arithmetic unit 42 and a ROI setting unit 45. The high intensity image determination unit 41 determines the average or sum of strength P from the sound ray data stored in the memory 50. Each strength P is a data value of each sound ray data. The high intensity image determination unit 41 sets a threshold value TH1 of the strength P and performs removal processing on the fundamental sound ray data that exceeds the threshold value TH1 and is determined to be a high intensity image. Also, the high intensity image determination unit 41 determines the average or sum of pixel values from the ultrasound image G generated by the image processor 30 based on the sound ray data. The high intensity image determination unit 41 sets a threshold value TH1 of each pixel value and removes image data exceeding the threshold value TH1 and determined to be a high intensity image. The detailed description of high intensity image determination unit 41 will be described later.

The ROI setting unit 45 sets a ROI (Region Of Interest) for an ultrasound image G.

The time intensity curve arithmetic unit 42 calculates the average, sum or maximum value of pixels values in the ROI that changes with time. The time intensity curve arithmetic unit 42 brings the calculated result to a graph and displays it through the display unit. Incidentally, the time intensity curve arithmetic unit 42 is also able to calculate the average, sum or maximum value of strength P using sound ray data corresponding to the ROI. The time intensity curve arithmetic unit 42 is used for the contrast echo using the ultrasound contrast agent. The contrast echo is principally performed on the heart and liver. Particularly when a time intensity curve is used, the contrast echo is mainly used in the liver. Therefore, although the following description is made of the liver, other regions to be examined can also be processed in like manner. Incidentally, the detailed description of time intensity curve arithmetic unit 42 will be explained later.

The memory 50 has an image memory that stores an image received at the transmit-receive unit 10, and a data memory that stores various data therein. The image memory includes an area in which each sound ray data is stored, and an area in which each ultrasound image G processed by the image processor 30 is stored. The area for storing the sound ray data includes a buffer which temporarily stores an image data set every frame. Thus, the image memory is capable of storing sound ray data corresponding to a predetermined frame rate, and an ultrasound image G therein. The image memory is also capable of recording a still image.

The controller 60 performs the general main control and processing of the ultrasound diagnostic apparatus 1.

High Intensity Image Determination Unit 41

The high intensity image determination unit 41 automatically removes image data of a high intensity image included in an ultrasound image G acquired at a desired frame rate or sound ray data set as its base. The high intensity image is generated from the motion of the liver due to the respiration of the subject or the motion of the heart close to the liver. Some or all of areas for the ultrasound image G are brought to a high intensity. Even where the position or angle of the operator's ultrasound probe 2 changes, some or all of the areas for the ultrasound image G may be high in intensity.

Figure 2:
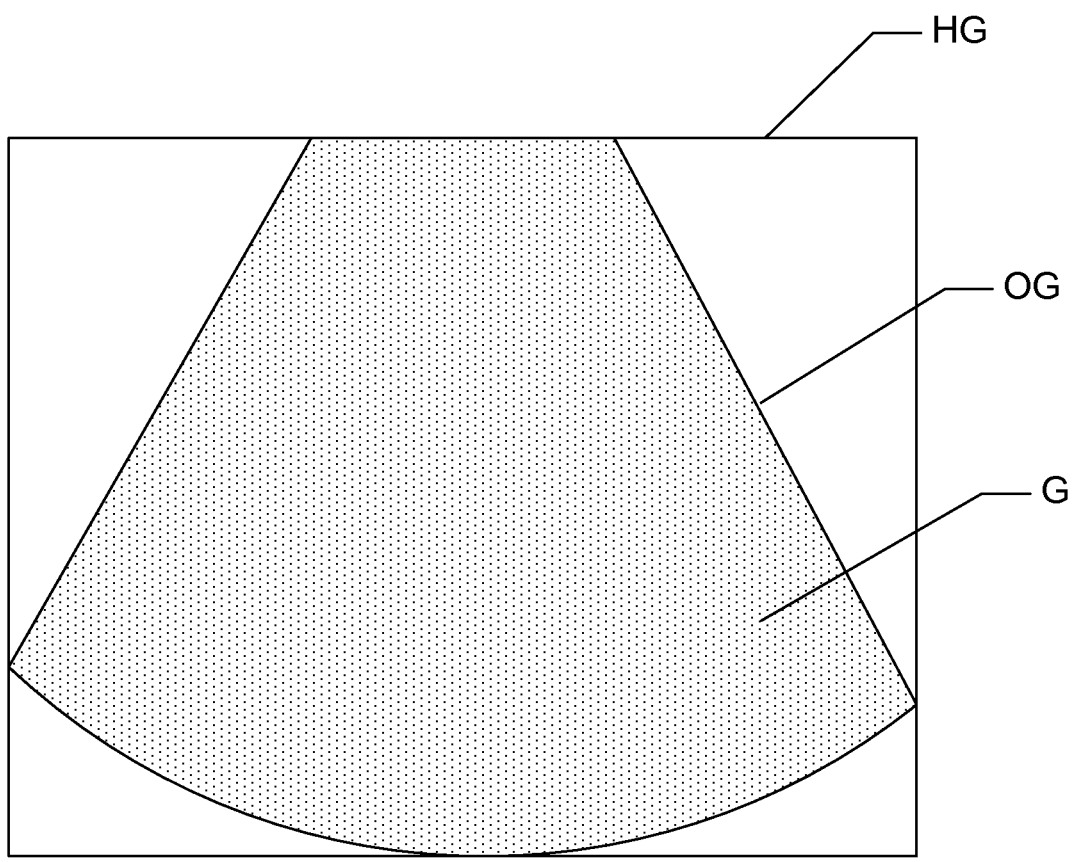
FIG. 2 is a diagram illustrating a display area HG and an ultrasound image G displayed on a display unit.

FIG. 2 is diagram showing the display unit 4. As shown in the drawing, a display area HG exists in the display unit 4. An ultrasound image G is displayed in the display area HG. The ultrasound image G forms a fan-shaped image display area OG. Incidentally, the image display area OG differs according to the ultrasound probe 2 to be used. Further, the image display area OG differs depending on a method of displaying the ultrasound image G, such as an enlarged display.

Normally, an inspection using an ultrasound contrast agent is performed to continuously acquire sound ray data while allowing a subject to hold his/her breath for a few seconds to a few tens of seconds. The breath holding is repeated within a predetermined time from a few times to a few tens of times to acquire sound ray data with time. As to the hemodynamics of the ultrasound contrast agent in the liver, for example, when the ultrasound contrast agent is injected into the body of the subject by intravenous injection, the hepatic artery of the liver is stained after about 10 to 15 seconds, and the portal vein in the liver is stained with a delay of a few seconds (3 to 5 seconds), so that the staining of the portal vein is given priority. The acquisition of sound ray data within about 3 minutes results in acquired images referred to as Vascular Imaging. Thereafter (after about ten minutes), the ultrasound contrast agent is captured in Kupffer cells in the liver to result in acquired images referred to as Kupffer Imaging.

Figure 3A:
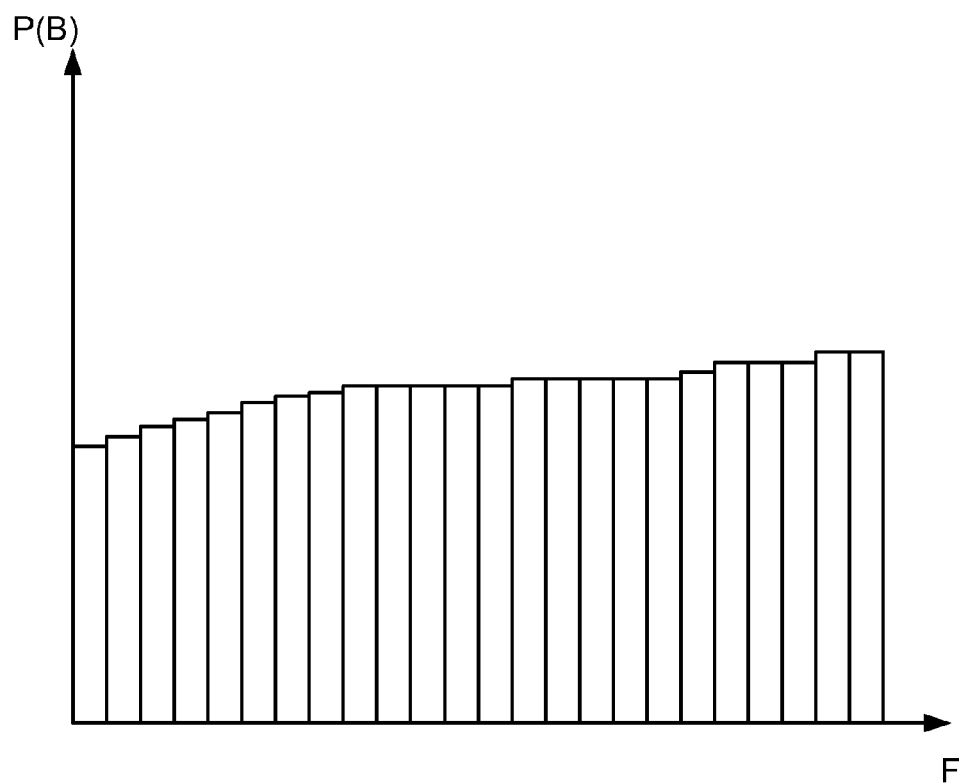
FIG. 3A shows the transition of strength P of sound ray data where a high intensity image is not included, and 3B shows the transition of strength P of sound ray data where a high intensity image is included.
Figure 3B:
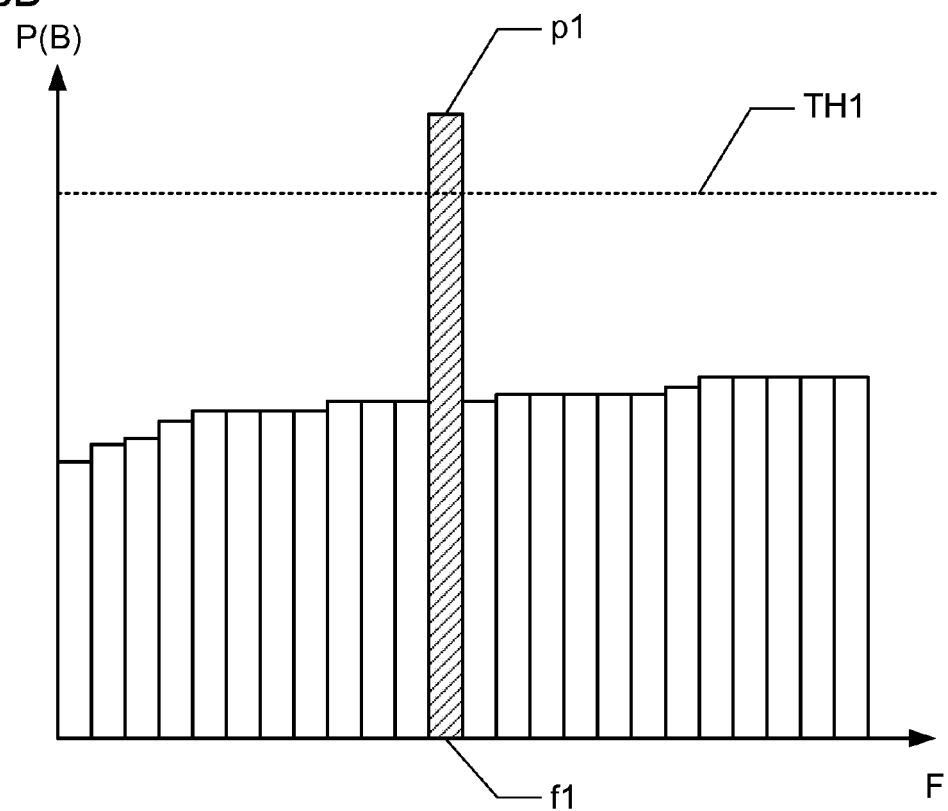

FIGS. 3A and 3B are graphs showing the strength P of sound ray data of consecutively acquired ultrasound images G assuming that an X axis is taken as a frame F (time) and a Y axis is taken as a strength P. Incidentally, one bar graph of the time base indicates a frame f, and the strength P of each sound ray data is shown in the length of the bar graph. The strength P of the sound ray data is equivalent to the average or sum of strength P in an image display area OG (whole area). The average of the strength P is shown in the Y axis of FIGS. 3A and 3B.

FIG. 3A shows the transition of strength P of sound ray data where a high intensity image is not included. FIG. 3B shows the transition of strength P of sound ray data where a high intensity image is included.

When the high intensity image is not mixed in as shown in FIG. 3A, the strength P of the sound ray data gradually increases with the inflow of an ultrasound contrast agent. When the high intensity image exists as shown in FIG. 3B, the strength P rises drastically. In FIG. 3B, the strength P assumes p1 in a frame f1 and exceeds a threshold value TH1.

The high intensity image determination unit 41 sets the threshold value TH1 of the strength P and automatically removes sound ray data at the frame f1 that exceeds the threshold value TH1. The threshold value TH1 is set in advance and can also be changed by an operator. A frame f of sound ray data to be eliminated is assigned an unused flag without deleting it to avoid its use other than when necessary to thereby remove from continuous received data.

The ultrasound image G is generated using the strength P of sound ray data and echo times. A pixel value B of the ultrasound image G is calculated from the strength P of the sound ray data. The high intensity image determination unit 41 is therefore capable of eliminating a high intensity image similarly even at not only the sound ray data but also at the ultrasound image G. The high intensity image determination unit 41 calculates the average or sum of pixel values B in the image display area OG (whole area) for every high intensity image of each frame f. The high intensity image determination unit 41 is capable of drawing or writing a graph of pixel values B of consecutively acquired ultrasound images G assuming the X axis shown in FIGS. 3A and 3B is taken as the frame F (time) and the Y axis shown therein is taken as the pixel value B. Likewise, the high intensity image determination unit 41 sets a threshold value TH1 of each pixel value B and automatically removes an ultrasound image G that exceeds the threshold value TH1. A flowchart for automatically removing an ultrasound image G exceeding the threshold value TH1 from sound ray data, and a flowchart for automatically removing an ultrasound image G exceeding the threshold value TH1 from ultrasound images G are shown below. The average of the pixel values B is shown in the Y axis of FIGS. 3A and 3B.

Flowchart of High Intensity Image Determination Unit 41

FIG. 4 is a flowchart of the high intensity image determination unit 41, which relates to sound ray data. Incidentally, FIG. 4 is shown inclusive of up to the generation of the ultrasound image G to provide easy understanding.

At Step S01, the high intensity image determination unit 41 acquires sound ray data corresponding to one frame stored in the image memory.

At Step S02, the high intensity image determination unit 41 calculates the strength P of sound ray data. The strength P corresponds to the average or sum equivalent to the image display area OG (whole area).

At Step S03, the high intensity image determination unit 41 determines whether the strength P of the sound ray data exceeds a set threshold value TH1. When the strength P thereof exceeds the threshold value TH1, the high intensity image determination unit 41 moves to Step S04. When the strength P thereof does not exceed the threshold value TH1, the high intensity image determination unit 41 moves to Step S05.

At Step S04, the high intensity image determination unit 41 applies an unused flag to the sound ray data having exceeded the threshold value TH1. Thereafter, the high intensity image determination unit 41 moves to Step S05 where the next sound ray data is acquired. The sound ray data is assigned the unused flag to avoid its usage at other than when necessary to thereby delete from consecutive received data.

At Step S05, the high intensity image determination unit 41 determines whether a frame f of sound ray data to be processed next exists. When the next frame f is found to exist, the high intensity image determination unit 41 moves to Step S01. When the next frame f is found not to exist, the high intensity image determination unit 41 moves to Step S06.

At Step S06, the high intensity image determination unit 41 applies a used flag to sound ray data (with no unused flag) not exceeding the threshold value TH1 and stores such sound ray data in the image memory.

At Step S07, the image processor 30 generates an ultrasound image G from the sound ray data with the used flag applied thereto. The image processor 30 applies a used flag to the generated ultrasound image G and stores the same in the image memory.

FIG. 5 is a flowchart of the high intensity image determination unit 41, which relates to an ultrasound image G. Incidentally, FIG. 5 is shown inclusive of up to the generation of the ultrasound image G to provide easy understanding as with FIG. 4.

At Step S11, the image processor 30 acquires sound ray data stored at the transmit-receive unit 10.

At Step S12, the image processor 30 generates a series of ultrasound images G from the sound ray data.

At Step S13, the high intensity image determination unit 41 acquires an ultrasound image G corresponding to one frame.

At Step S14, the high intensity image determination unit 41 calculates a pixel value B of an ultrasound image G. The pixel value B indicates the average or sum equivalent to an image display area OG (whole area).

At Step S15, the high intensity image determination unit 41 determines whether the pixel value B exceeds a set threshold value TH1. When the pixel value B is found to exceed the threshold value TH1, the high intensity image determination unit 41 moves to Step S16. When the pixel value B is found not to exceed the threshold value TH1, the high intensity image determination unit 41 moves to Step S17.

At Step S16, the high intensity image determination unit 41 applies an unused flag to the ultrasound image G having exceeded the threshold value TH1. Thereafter, the high intensity image determination unit 41 moves to Step S17. The ultrasound image G is assigned the unused flag to avoid its usage at other than when necessary to thereby delete from consecutive received data.

At Step S17, the high intensity image determination unit 41 determines whether a frame f of an ultrasound image G to be processed next exists. When the next frame f is found to exist, the high intensity image determination unit 41 moves to Step S13. When the next frame f is found not to exist, the high intensity image determination unit 41 moves to Step S18.

At Step S18, the high intensity image determination unit 41 applies a used flag to an ultrasound image with no unused flag and stores such an ultrasound image in the image memory.

As is understood from the above-described flowcharts, the high intensity image determination unit 41 is capable of processing at high speed because the number of process steps related to the flowchart shown in FIG. 4 is reduced and the calculation method is also simple.

Time Intensity Curve Arithmetic Unit 42

As to a time intensity curve, the time intensity curve arithmetic unit 42 calculates a time intensity curve in a ROI (Region Of Interest) set by the ROI setting unit 45 using the ultrasound image G with the used flag applied by the high intensity image determination unit 41. Incidentally, the ultrasound image G with the unused flag applied thereto is invoked as needed and can be referred to by an operator. The time intensity curve arithmetic unit 42 does not make use of the frame (called unused frame) with the unused flag applied by the high intensity image determination unit 41. The time intensity curve arithmetic unit 42 interpolates pixel values B of adjacent frames f with respect to the unused frame having no pixel value B to calculate a time intensity curve.

FIG. 6 is a flowchart of the series of contrast echoes and the time intensity curve arithmetic unit 42.

At Step S21, the operator operates the ultrasound diagnostic apparatus 1 to set it to a contrast mode through the signal processor 20.

At Step S22, the operator or helper injects an ultrasound contrast agent into the subject.

At Step S23, the operator operates the ultrasound diagnostic apparatus 1 to start the acquisition of sound ray data. The sound ray data are stored in the image memory.

At Step S24, the operator ends the acquisition of a series of ultrasound images G.

At Step S25, the ultrasound diagnostic apparatus 1 eliminates a high intensity image through the use of the high intensity image determination unit 41. As described above, the high intensity image determination unit 41 applies an unused flag to the sound ray data of the high intensity image or the high intensity image.

At Step S26, the operator observes the acquired ultrasound image G using the ROI setting unit 45 to set a ROI. The ROI is set based on an arbitrary position and size by using the time intensity curve arithmetic unit 42. Although the ROI is normally set after the acquisition of the ultrasound images G, it may be set during the acquisition thereof. The ROI may be set at one point or plural points.

At Step S27, the time intensity curve arithmetic unit 42 calculates a time intensity curve from an ultrasound image G to which no unused flag is applied. The time intensity curve arithmetic unit 42 interpolates pixel values B of adjacent frames f with respect to an unused frame having no pixel value B to calculate a time intensity curve. As a method of interpolation by the time intensity curve arithmetic unit 42, linear interpolation or polynomial interpolation or the like is used.

At Step S28, the time intensity curve arithmetic unit 42 causes the display unit 4 to display the time intensity curve thereon. The operator observes the time intensity curve displayed on the display unit 4.

Figure 7:
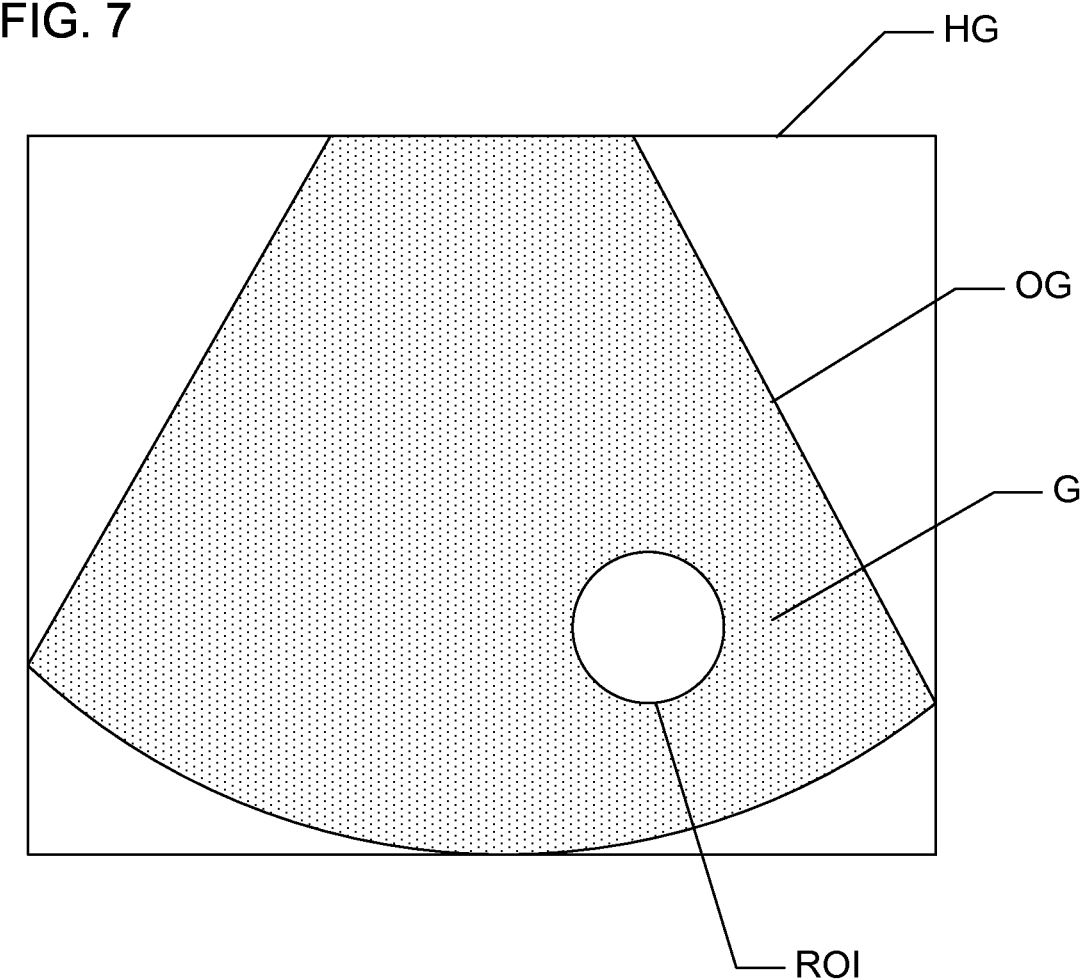
FIG. 7 is a diagram showing a ROI set in an ultrasound image G.

FIG. 7 is a diagram showing a ROI set in an ultrasound image G. The ROI is normally set to within the ultrasound image G. The position, shape and size of the ROI can arbitrarily be changed by the operator, and the operator sets a desired area.

Figure 8A:
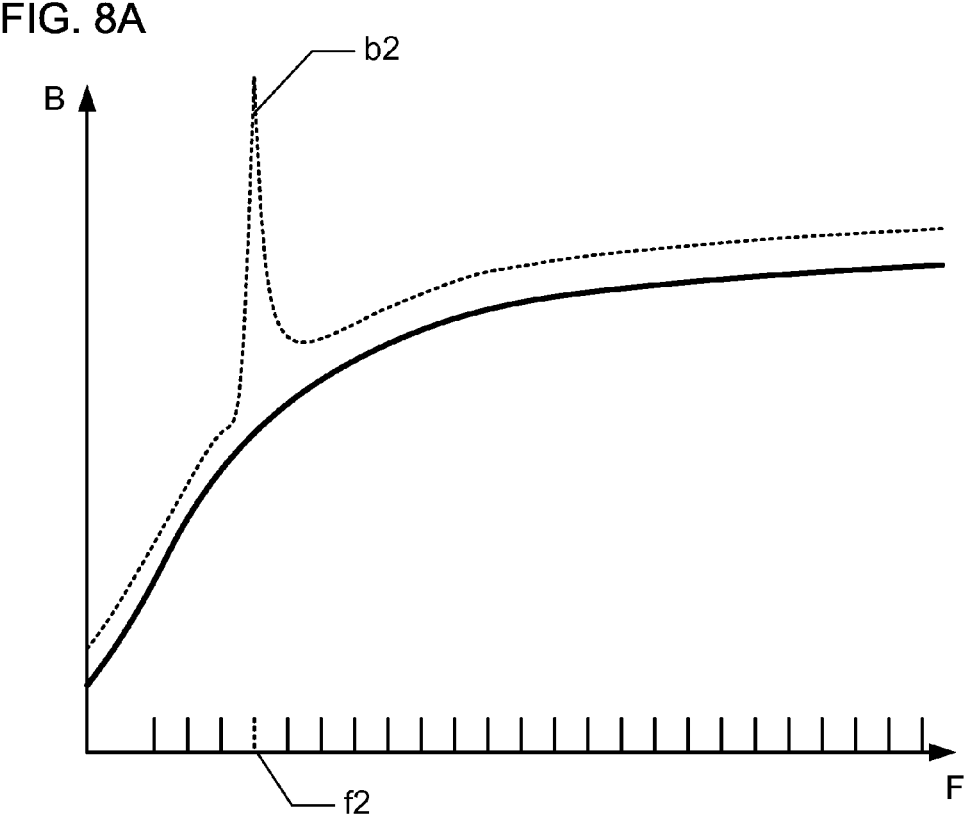
FIG. 8A is a diagram showing a result of calculation of an average pixel value of a ROI, which has been shown in time intensity curves indicated by a broken line and a solid line.
Figure 8B:
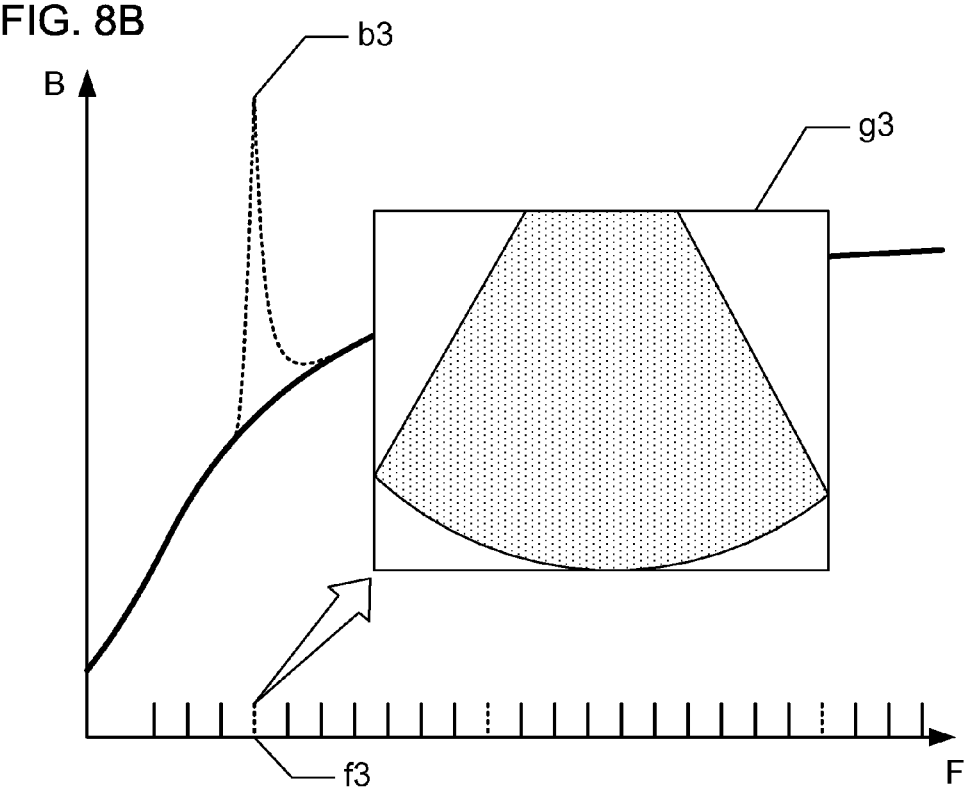
FIG. 8B is diagram showing a result of calculation of an average pixel value of a ROI, which has been shown in time intensity curves indicated by a broken line and a solid line and shown by an ultrasound image.

FIGS. 8A and 8B are diagrams showing an average pixel value of an ROI. Incidentally, the time intensity curve arithmetic unit 42 is capable of measuring the average, sum or maximum value of pixel values B of the ROI. The will be explained using a method for calculating the average of the pixel values B of the ROI.

FIG. 8A is a time intensity curve in which the average pixel value of a ROI has been calculated assuming that an X axis is a frame F (time) and a Y axis is a pixel value B. A graph shown in FIG. 8A is displayed on the display unit 4, and the operator is able to observe it. Since no high intensity image is included in the time intensity curve, a smooth curve drawn in a solid line is plotted. The time intensity curve arithmetic unit 42 interpolates pixel values B of adjacent frames f with respect to an unused frame having no pixel value B to calculate a time intensity curve.

FIG. 8B is a time intensity curve in which the average pixel value of a ROI has been calculated assuming that an X axis is a frame F (time) and a Y axis is a pixel value B as with FIG. 8A. As shown in FIG. 8B, a frame f3 being a scale for an unused frame is indicated by a broken line. When the operator clicks the frame f3, the time intensity curve arithmetic unit 42 causes an ultrasound image g3 and a pixel value b3 corresponding to the frame f3 to be displayed. The ultrasound image g3 can be displayed in scale-down or normal form.

FIG. 8(b) is a time intensity curve in which the average pixel value of a ROI has been calculated assuming that an X axis is a frame F (time) and a Y axis is a pixel value B as with FIG. 8(a). As shown in FIG. 8(b), a frame f3 being a scale for an unused frame is indicated by a broken line. When the operator clicks the frame f3, the time intensity curve arithmetic unit 42 causes an ultrasound image g3 and a pixel value b3 corresponding to the frame f3 to be displayed. The ultrasound image g3 can be displayed in scale-down or normal form.

As shown in FIGS. 8A and 8B, the time intensity curve arithmetic unit 42 is capable of displaying an ultrasound image G of an unused frame, or a time intensity curve and a pixel value B according to an operator's desire. The operator is therefore able to confirm the need for the unused frame or its influence degree.

Second Embodiment

In a high intensity image, the ultrasound image G may not necessarily only be a case where the entire ultrasound image G becomes high in intensity, but may be a case where only a partial area becomes high in intensity. Even when a high intensity image exists in a partial area of the ultrasound image G, a high intensity image determination unit 41 of a second embodiment automatically eliminates the ultrasound image G. Since an ultrasound diagnostic apparatus 1 according to the second embodiment is similar in configuration to the first embodiment, the same reference numerals are used therein. Different points will be explained below.

Figure 9A:
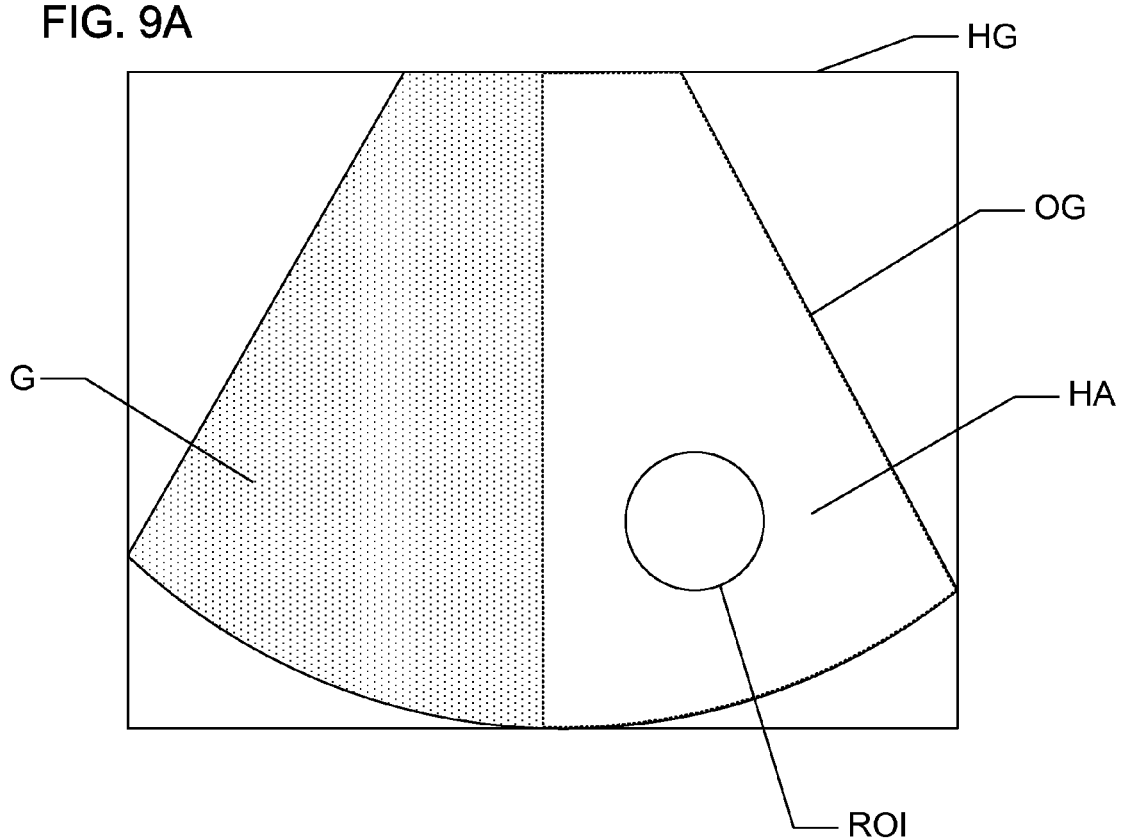
FIG. 9A is a diagram showing a case where a high intensity area HA exists in a partial area of an acquired ultrasound image G.
Figure 9B:
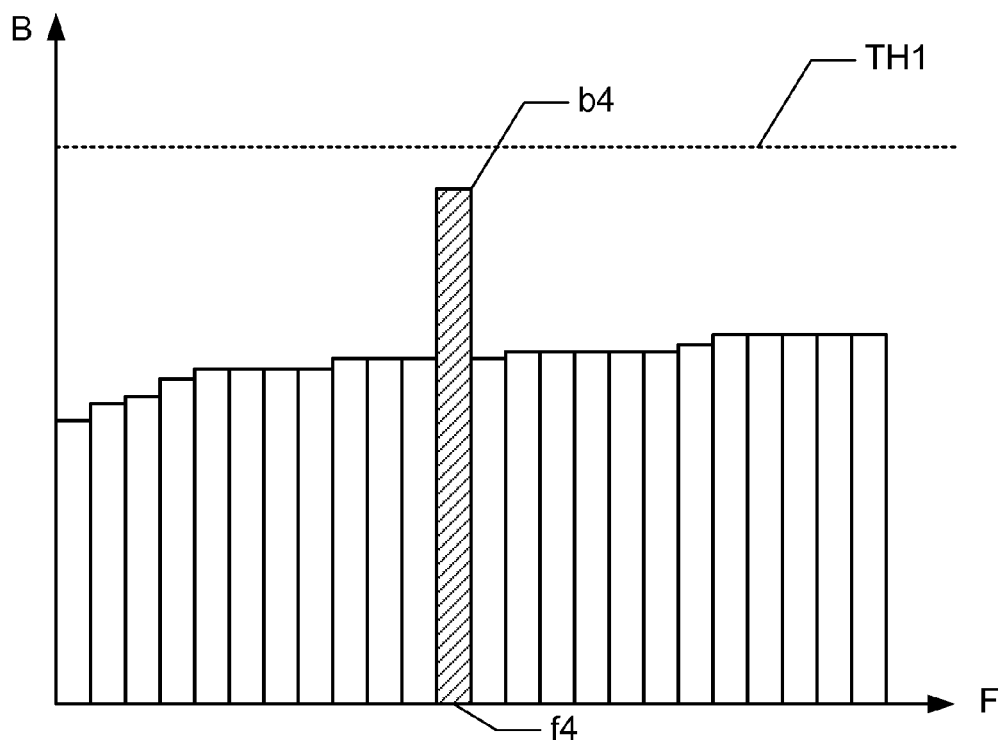
FIG. 9B is a diagram showing a pixel value which does not exceed a threshold value TH1.
Figure 10:
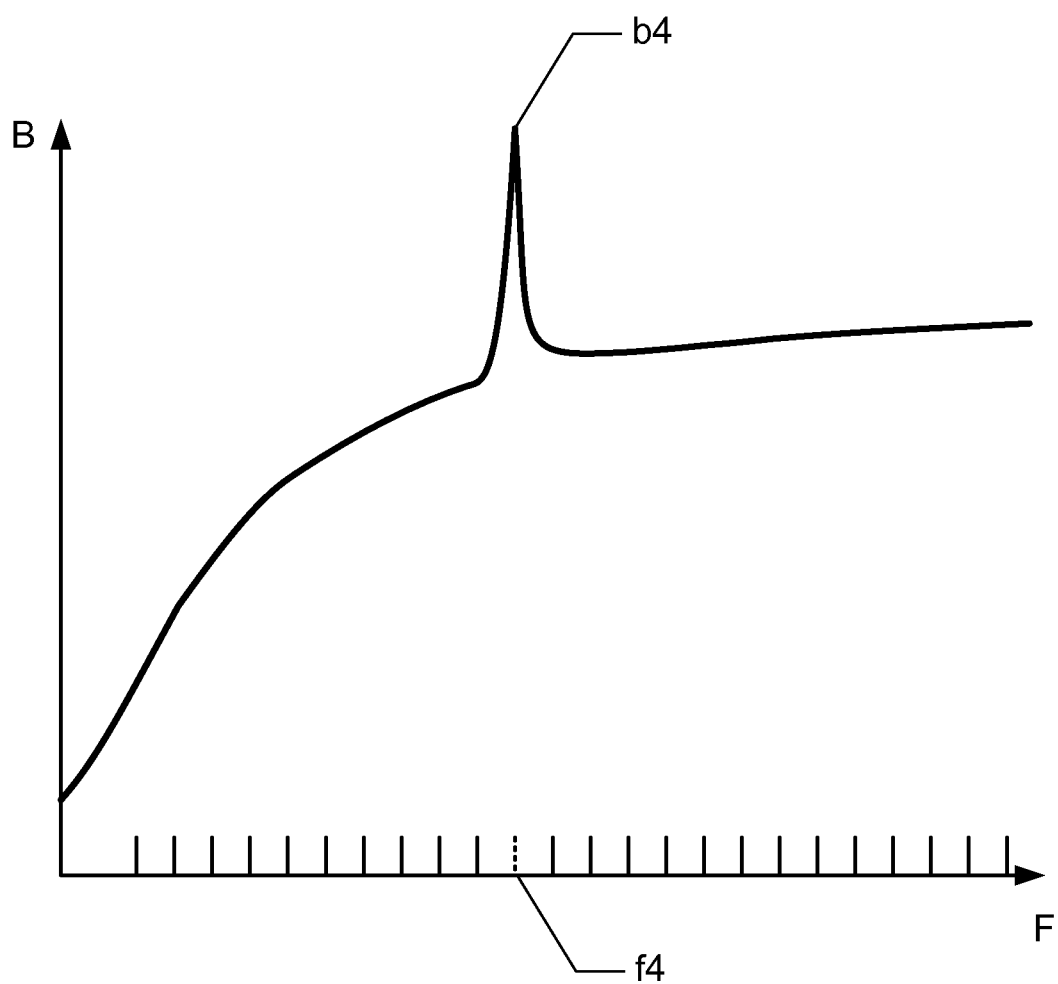
FIG. 10 is a diagram illustrating a sawtooth time intensity curve.

FIG. 9A is a diagram showing a case in which a high intensity area HA exists in a partial area of an acquired ultrasound image G. Assume that an ultrasound image G having a high intensity area HA that exists in such a right half as shown in the drawing exists in a sampling of a frame f4 of the acquired ultrasound image G. Since the high intensity image determination unit 41 of the first embodiment measures the intensity over the entire area of the ultrasound image G, the intensity of the frame f reaches a pixel value b4 and does not exceed a threshold value TH1 as shown in FIG. 9B. Therefore, when a ROI is set to the high intensity area, a time intensity curve becomes the pixel value b4 at the frame f4 and assumes a sawtooth shape as shown in FIG. 10.

The high intensity image determination unit 41 of the present embodiment segments the write or drawing area of the ultrasound image G into plural forms. When high intensity areas that exceed a plurality of threshold values TH1 exist in the areas segmented into the plural form, the high intensity image determination unit 41 automatically removes them as unused frames. A detailed description thereof will be made below.

Figure 11:
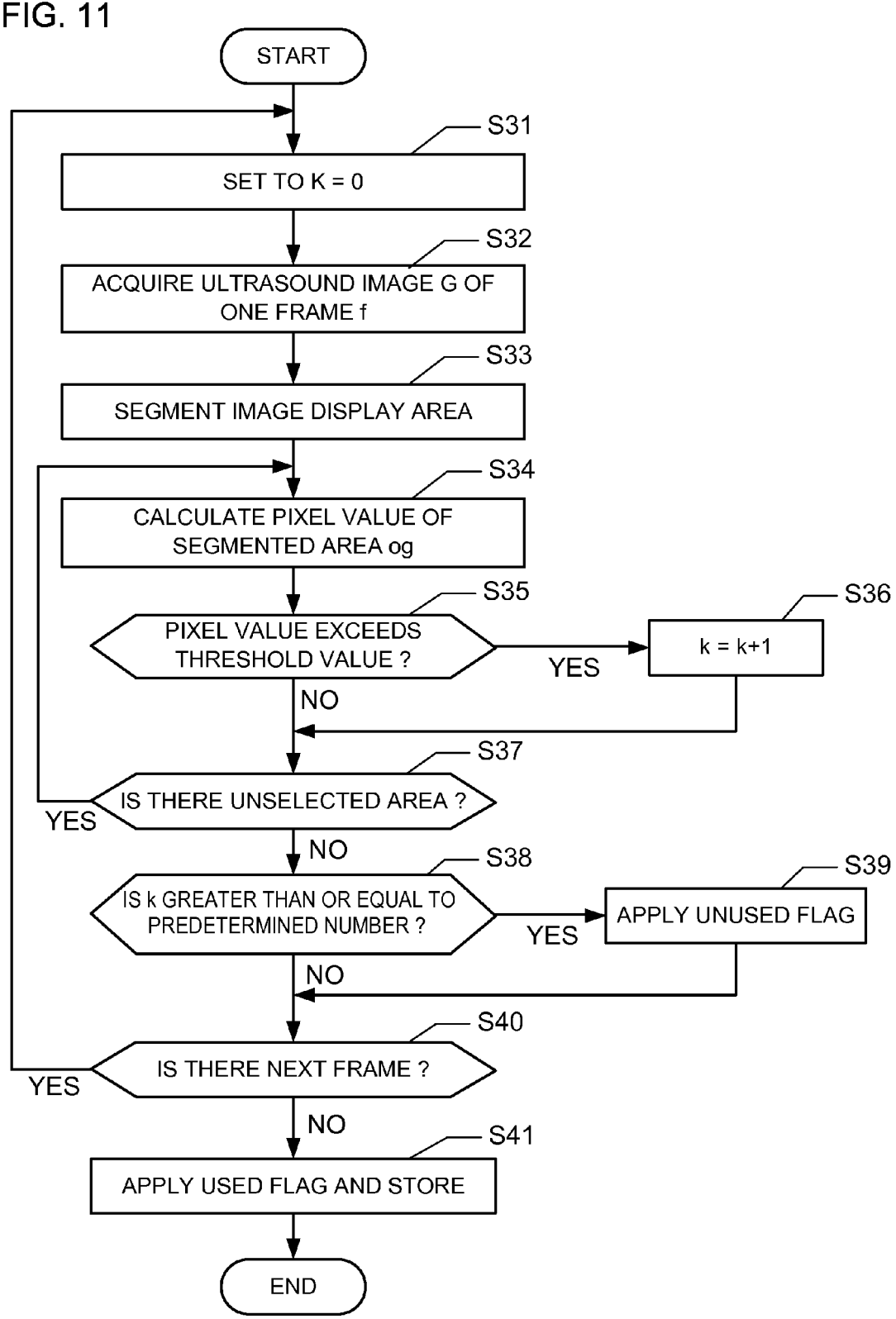
FIG. 11 is a flowchart of the high intensity image determination unit using segmented areas og.

FIG. 11 is a flowchart of the high intensity image determination unit 41 using each segmented area og.

At Step S31, the high intensity image determination unit 41 sets a counter k to 0.

At Step S32, the high intensity image determination unit 41 acquires an ultrasound image G of one frame.

Figure 12A:
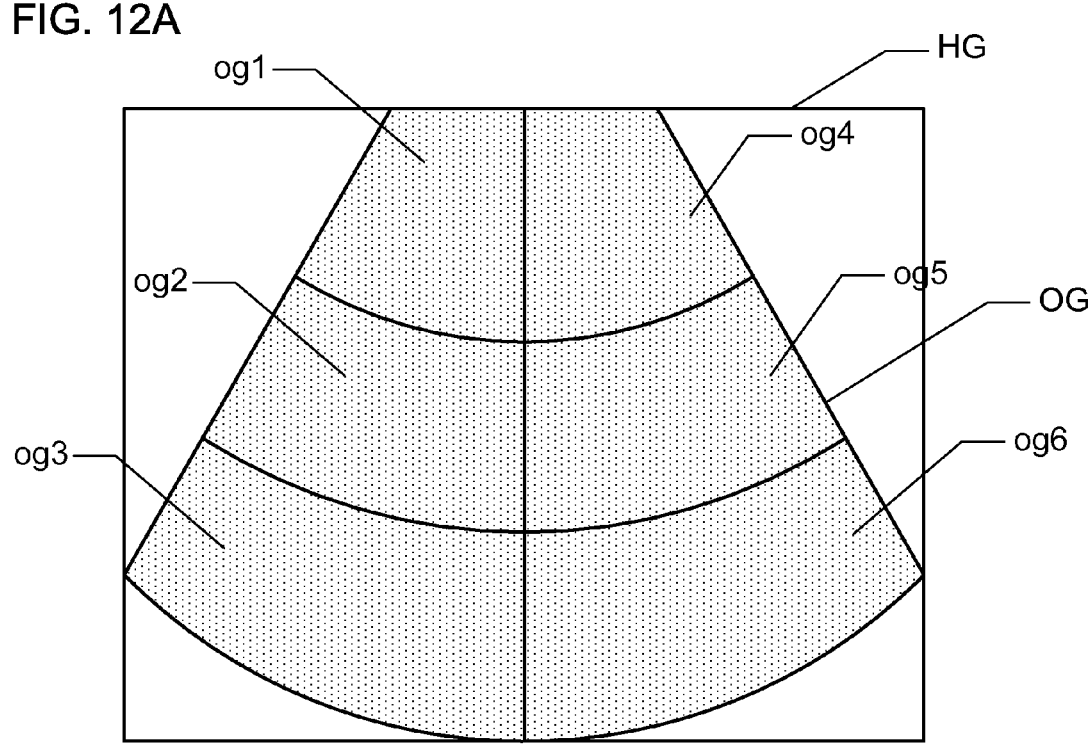
FIG. 12A is a diagram showing an image display area OG segmented into six.

At Step S33, the high intensity image determination unit 41 segments an image display area OG of the ultrasound image G into a predetermined number of segmented areas og. FIG. 12A shows where the image display area OG is segmented into six. As shown in the drawing, the image display area OG is divided or segmented into a first segmented area og1 through a sixth segmented area og6. The high intensity image determination unit 41 provides segmentation into six, but enables segmentation into an arbitrary number of areas.

Referring back to FIG. 11, at Step S34, the high intensity image determination unit 41 selects one of the segmented areas og divided in the form of the predetermined number and calculates pixel values in the selected area. The pixel values of the segmented area og are used to calculate the average or sum thereof in that area.

At Step S35, the high intensity image determination unit 41 determines whether a pixel value exceeds a set threshold value TH1. When it is found to exceed the threshold value TH1, the high intensity image determination unit 41 moves to Step S36. When it is found not to exceed the threshold value TH1, the high intensity image determination unit 41 moves to Step S37.

At Step S36, the high intensity image determination unit 41 adds 1 to the counter k.

At Step S37, the high intensity image determination unit 41 determines whether an unselected area exists in each segmented area og. When the unselected area is found to exist, the high intensity image determination unit 41 moves to Step S34. When the unselected area is found not to exist, the high intensity image determination unit 41 moves to Step S38.

At Step S38, the high intensity image determination unit 41 determines whether the counter k is a predetermined number or more. When the counter k is found to be the predetermined number or more, the high intensity image determination unit 41 moves to Step S39. When the counter k is found to be smaller than the predetermined number, the high intensity image determination unit 41 moves to Step S40. The predetermined number of the counter k has been set in advance, and the number thereof can be changed by the operator. Incidentally, the predetermined number can be selected as being less than or equal to the number of divisions. In the case of the six divisions, Nos. 1 through 6 can be selected.

At Step S39, the high intensity image determination unit 41 applies an unused flag to a captured ultrasound image G. Thereafter, the high intensity image determination unit 41 moves to Step S40. An ultrasound image G to be removed is assigned an unused flag to avoid its usage except when necessary and is thereby eliminated from consecutive received data.

At Step S40, the high intensity image determination unit 41 determines whether a frame f of an ultrasound image G to be processed next exists. When the next frame f is found to exist, the high intensity image determination unit 41 moves to Step S31. When the next frame f is found not to exist, the high intensity image determination unit 41 moves to Step S41.

At Step S41, the high intensity image determination unit 41 applies a used flag to an ultrasound image G with no unused flag and stores it in the corresponding image memory.

Modification

In FIG. 9A, when the ROI is set to other than the high intensity area HA, no influence is exerted on the time intensity curve. It is therefore not necessary to remove the frame f4 as the unused frame. A high intensity image determination unit 41 of the present modification segments a write or drawing area of an ultrasound image G into plural forms and calculates an unused frame by using an area not including the ROI or an area included in the ROI. A detailed description thereof will be made below.

Figure 12B:
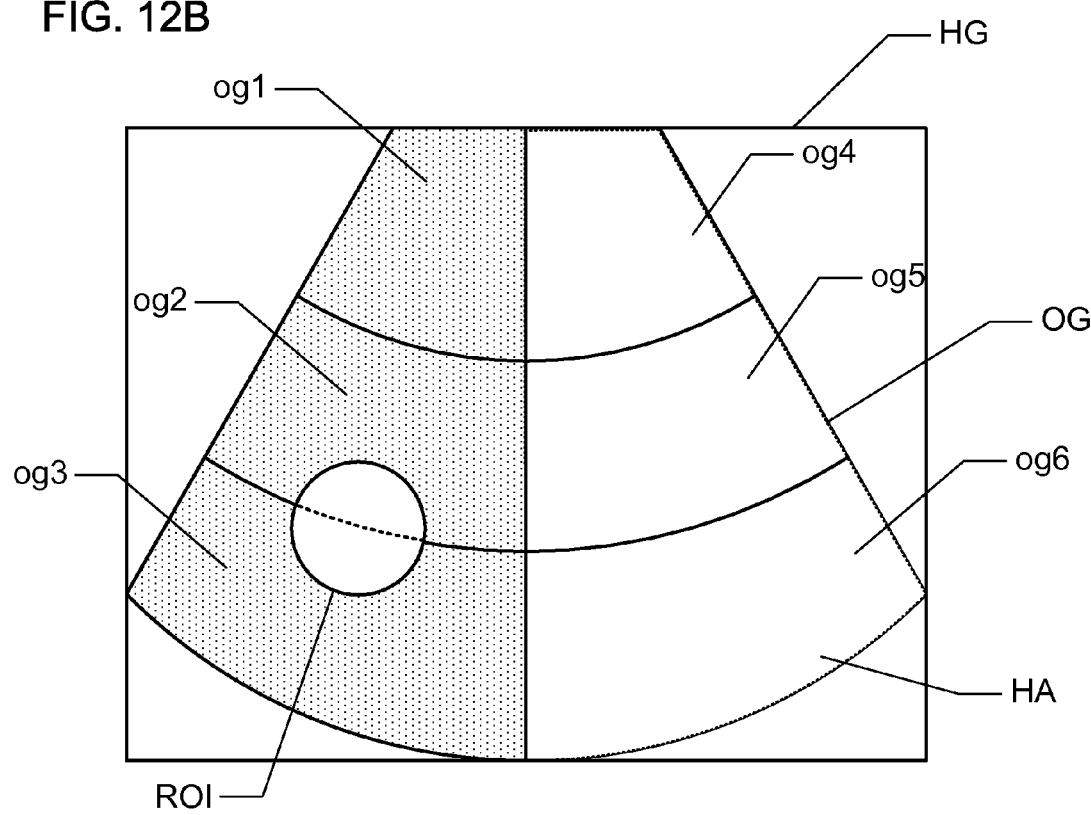
FIG. 12B is a diagram showing a case in which a high intensity area HA exists in the right half of an area in which the image display area OG is segmented into six.

FIG. 12B is a diagram showing a case in which a high intensity area HA exists in the right half of an area in which an image display area OG is segmented into six. As shown in the drawing, a ROI is set to a second segmented area og2 and a third segmented area og3. In the present modification, the ROI is set by a time intensity curve arithmetic unit 42 and thereafter the removal of a high intensity image by the high intensity image determination unit 41 is performed.

Figure 13:
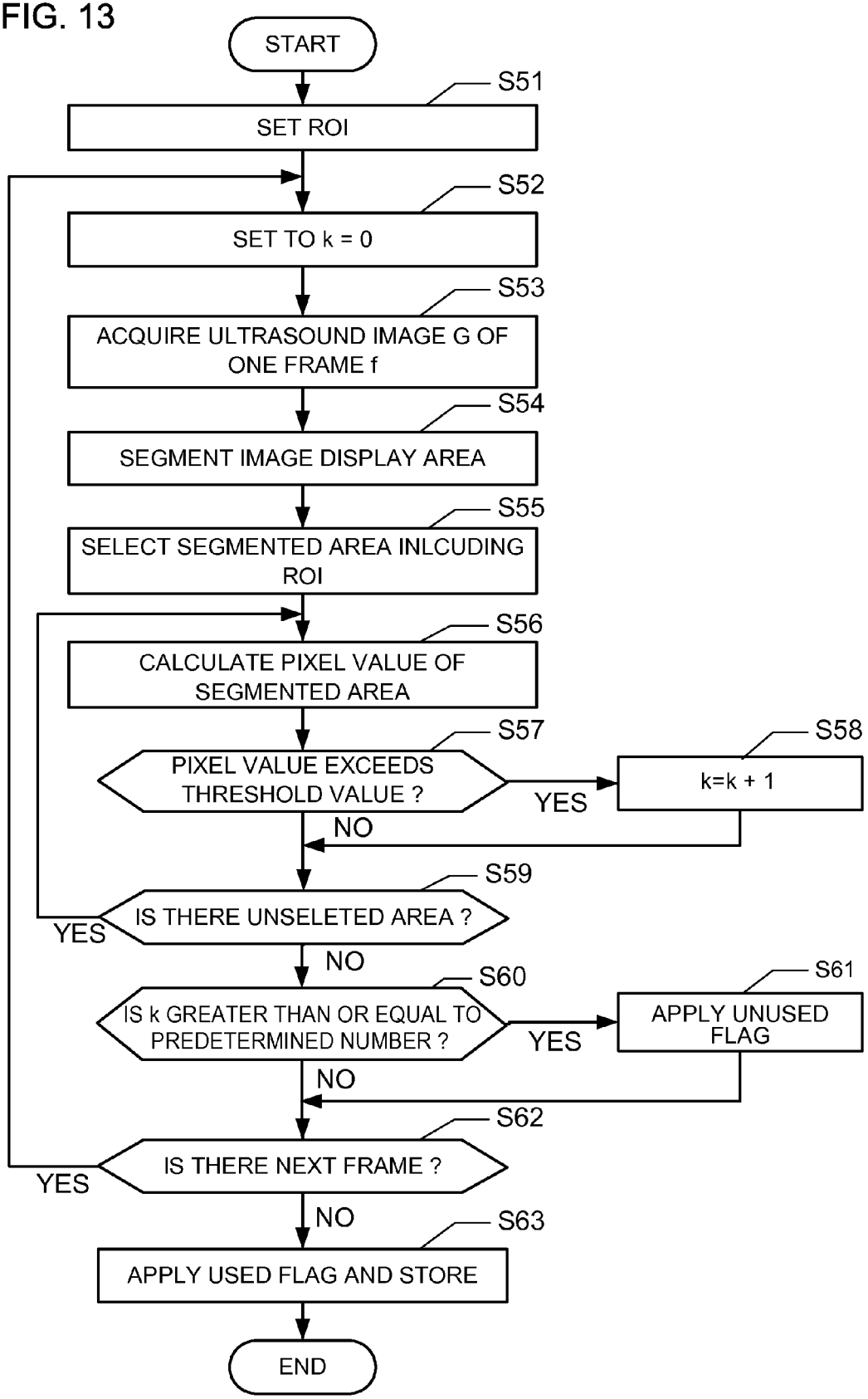
FIG. 13 is a flowchart of the high intensity image determination unit which relates to an area including a ROI.

FIG. 13 is a flowchart of the high intensity image determination unit 41 in the area that includes the ROI.

At Step S51, the operator sets a ROI using a ROI setting unit 54.

At Step S52, the high intensity image determination unit 41 sets a counter k to 0.

At Step S53, the high intensity image determination unit 41 acquires an ultrasound image G of one frame f.

At Step S54, the high intensity image determination unit 41 segments an image display area OG of an ultrasound image G into a predetermined number of segmented areas og. Here, as shown in FIG. 12B, the image display area OG is divided into six. As the number of divisions of the image display area OG, the image display area OG can be segmented into an arbitrary number of areas.

Referring back to FIG. 13, at Step S55, the high intensity image determination unit 41 calculates the number of areas where the segmented areas og and the ROI overlap, and the corresponding areas. Since the second segmented area og2 and the third segmented area og3 overlap with the ROI here, the number of areas is 2 and the corresponding areas become the second segmented area og2 and the third segmented area og3.

At Step S56, the high intensity image determination unit 41 selects one of the corresponding segmented areas og and calculates pixel values of the selected area. The pixel values of the segmented area og are used to calculate the average or sum thereof in the segmented area.

At Step S57, the high intensity image determination unit 41 determines whether a pixel value exceeds a set threshold value TH1. When it is found to exceed the threshold value TH1, the high intensity image determination unit 41 moves to Step S58. When it is found not to exceed the threshold value TH1, the high intensity image determination unit 41 moves to Step S59.

At Step S58, the high intensity image determination unit 41 adds 1 to the counter k.

At Step S59, the high intensity image determination unit 41 determines whether an unselected area exists in the corresponding areas of the segmented areas og. When the unselected area is found to exist, the high intensity image determination unit 41 moves to Step S56. When the unselected area is found not to exist, the high intensity image determination unit 41 moves to Step S60.

At Step S60, the high intensity image determination unit 41 determines whether the counter k is greater than or equal to a predetermined number. Although the number of the areas that overlap with the ROI is 2 here, the high intensity image determination unit 41 determines whether the counter k is greater than or equal to 1, for example. When the counter k is found to be greater than or equal to 1, the high intensity image determination unit 41 moves to Step S61. When the counter k is found to be smaller than 1, the high intensity image determination unit 41 moves to Step S62. When even one of areas that exceed the threshold value TH1 exists in the areas that overlap with the ROI, the high intensity image determination unit 41 does not use a frame thereof by setting the counter k to 1.

At Step S61, the high intensity image determination unit 41 applies an unused flag to a captured ultrasound image G. Thereafter, the high intensity image determination unit 41 moves to Step S62.

At Step S62, the high intensity image determination unit 41 determines whether a frame f of an ultrasound image G be processed next exists. When the next frame f is found to exist, the high intensity image determination unit 41 moves to Step S52. When the next frame f is found not to exist, the high intensity image determination unit 41 moves to Step S63.

At Step S63, the high intensity image determination unit 41 applies a used flag to an ultrasound image G with no unused flag applied thereto and stores it in the image memory.

According to the present modification, when the high intensity image exists in the set area of ROI, the high intensity image determination unit 41 sets its frame f to be unused. When no high intensity image exists in the set area of ROI, the high intensity image determination unit 41 is capable of using the frame f. Thus, as the time intensity curve calculated at the time intensity curve arithmetic unit 42, a smooth curve that is low in the lack of the frame f can be drawn. Incidentally, the time intensity curve arithmetic unit 42 interpolates the pixel values of adjacent frames f with respect to each unused frame with no pixel value to calculate a time intensity curve.

Third Embodiment

A description will be made of a method in which a high intensity image determination unit 41 of a third embodiment removes a high intensity image that does not reach the above-described threshold value TH1. Since an ultrasound diagnostic apparatus 1 according to the third embodiment is similar in configuration to the first embodiment, the same reference numerals are used. Different points will be explained below.

Figure 14A:
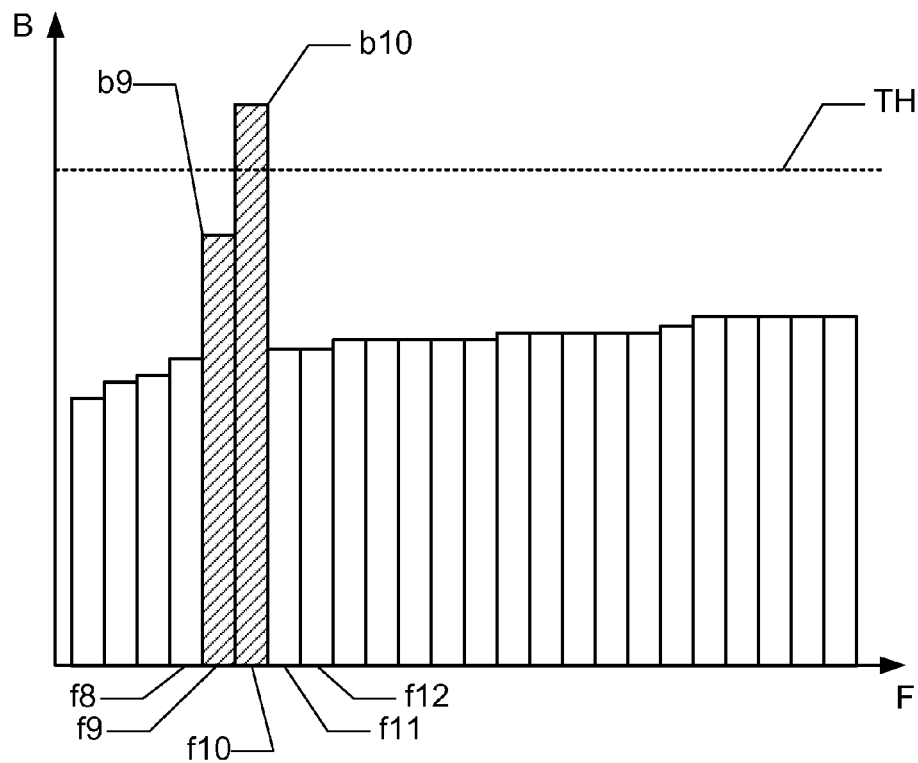
FIGS. 14A and 14B are diagrams showing the manner in which high intensity images consecutively appear in continuous frames f.
Figure 14B:
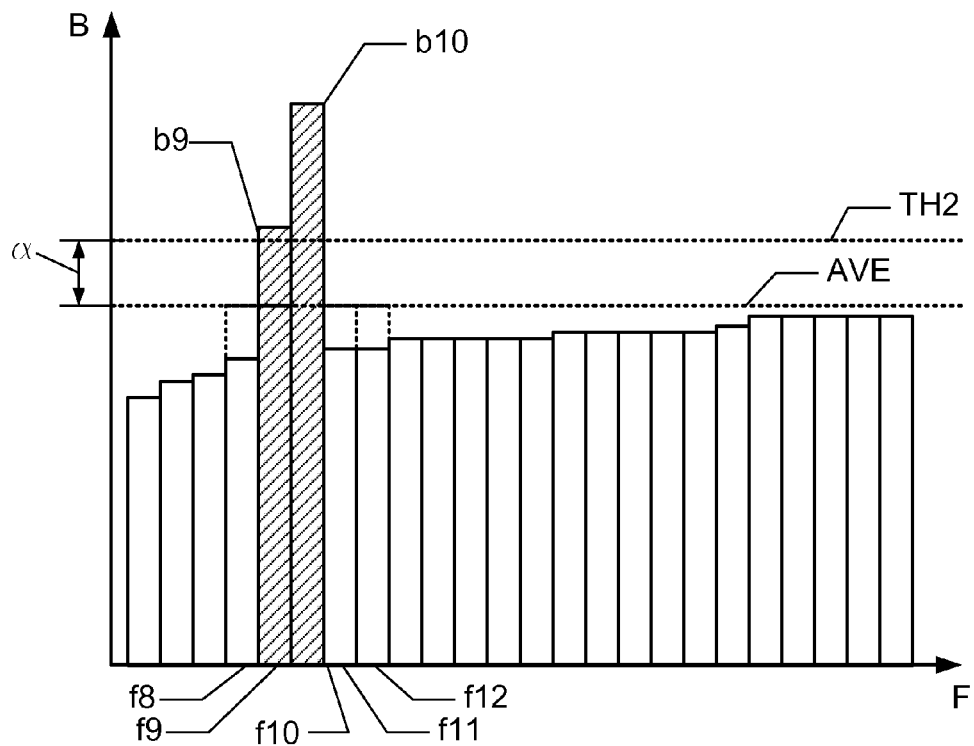

High intensity images may occur in not only one frame f shown in each of the first and second embodiments, but also in a sequence of plural frames f. FIGS. 14A and 14B are diagrams in which high intensity images continuously appear at a sequence of frames f. In FIGS. 14A and 14B, an X axis is assumed to be a frame F (time), and a Y axis is assumed to be a pixel value B. The number of frames at which high intensity images appear continuously, is 2 frames f or so upon the contrast echo although it depends on the frame rate. When there is such a frame f that a pixel value exceeds a threshold value TH1 at a frame f10 as shown in FIG. 14A, for example, such a frame f9 that a pixel value does not exceed the threshold value TH1 may exist.

As shown in FIG. 14B, the high intensity image determination unit 41 of the present embodiment determines the average value AVE of pixel values of frames f8 through f12, using two frames f lying prior to and subsequent to the frame f10, sets a threshold value TH2 obtained by adding an incremental quantity α to the average value AVE, and detects each frame f that exceeds the threshold value TH2.

There are known a method of setting the incremental quantity α as a fixed value, and a method of setting it as a variable value like 30% or the like of the average AVE.

Figure 15:
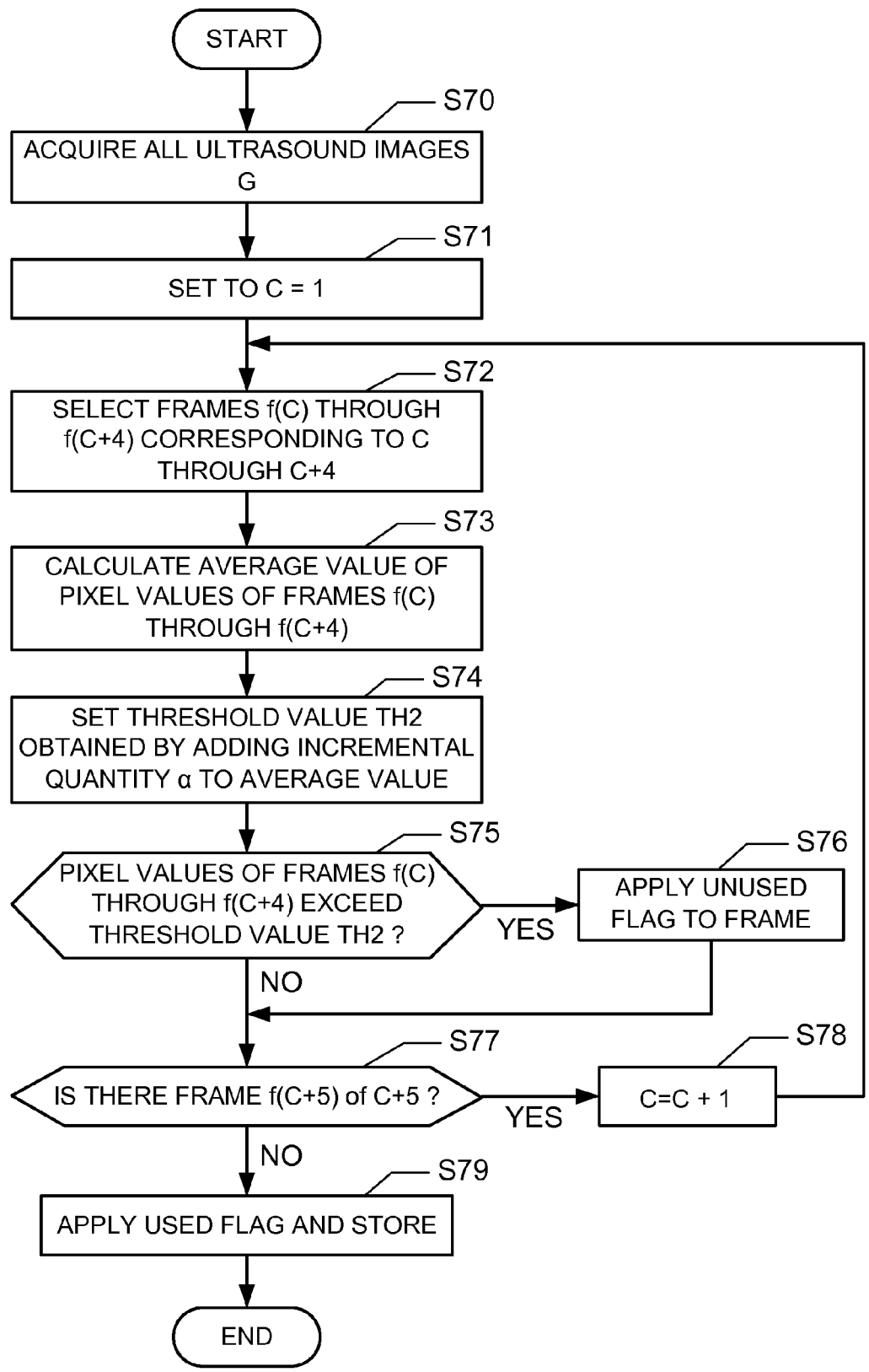
FIG. 15 is a flowchart for removing a high intensity image from a pixel value of a frame f.

FIG. 15 is a flowchart for eliminating a high intensity image from an average pixel value of a frame f. Incidentally, the present flowchart will be explained where the average value AVE of pixel values of five frames f is used.

At Step S70, the high intensity image determination unit 41 reads all ultrasound images G to be analyzed by a time intensity curve arithmetic unit 42.

At Step S71, the high intensity image determination unit 41 sets a counter C to 1.

At Step S72, the high intensity image determination unit 41 selects frames f(C) through f(C+4) corresponding to the counters C through C+4.

At Step S73, the high intensity image determination unit 41 calculates pixel values of the frames f(C) through f(C+4) and calculates the average value AVE of the pixel values.

At Step S74, the high intensity image determination unit 41 sets a threshold value TH2 (refer to FIG. 14B) obtained by adding an incremental quantity α to the average value AVE. The incremental quantity α is set as a fixed value or a variable value.

At Step S75, the high intensity image determination unit 41 determines whether the respective pixel values of the frames f(C) through f(C+4) exceed the threshold value TH2. The high intensity image determination unit 41 moves to Step S76 with respect to each frame f that exceeds the threshold value TH2. The high intensity image determination unit 41 moves to Step S77 with respect to each frame f that does not exceed the threshold value TH2.

At Step S76, the high intensity image determination unit 41 applies an unused flag to the corresponding frame f that exceeds the threshold value TH2. Thereafter, the high intensity image determination unit 41 moves to Step S77.

At Step S77, the high intensity image determination unit 41 determines whether a frame f (C+5) of a counter C+5 exists. When the frame f (C+5) is found to exist, the high intensity image determination unit 41 moves to Step S78. When the frame f (C+5) is found not to exist, the high intensity image determination unit 41 moves to Step S79.

At Step S78, the high intensity image determination unit 41 adds 1 to the counter C. Thereafter, the high intensity image determination unit 41 moves to Step S72.

At Step S79, the high intensity image determination unit 41 applies a used flag to a frame f with no unused flag applied thereto and stores the same in the image memory.

Although the high intensity image determination unit 41 of the present embodiment has determines each frame f to be removed, using the average value AVE of the pixel values of the five frames f, the three frames f or more may be used as the number of frames for calculating the average value AVE.

Modification

Although the average value AVE of the pixel values has been calculated with respect to all the frames fin the third embodiment, frames f lying prior to and subsequent to the frame f that exceeds the threshold value TH1 shown in the first embodiment are used. Incidentally, the present modification will also be explained where the average value AVE of the pixel values of the five frames is used.

Figure 16:
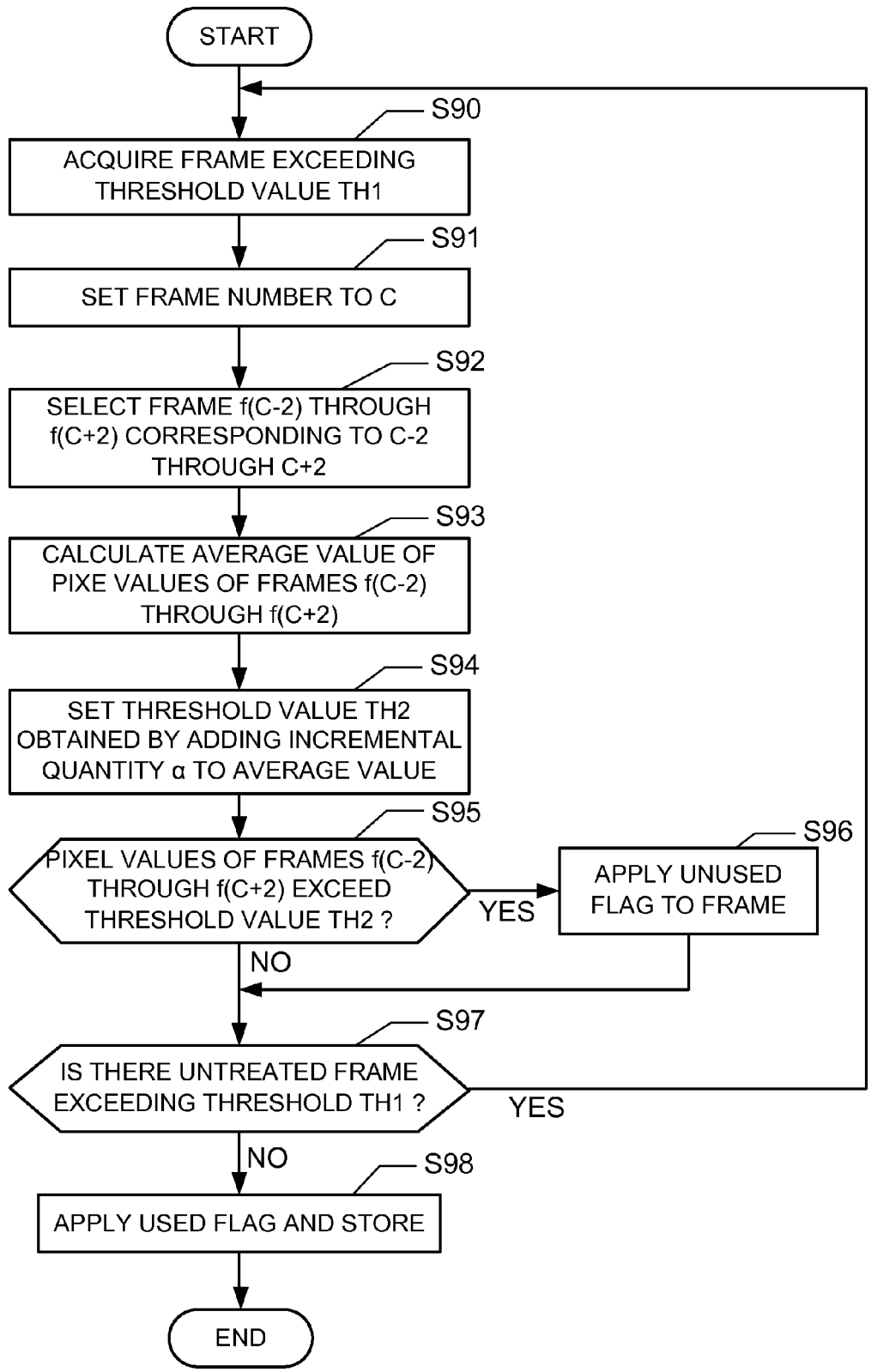
FIG. 16 is a flowchart for removing a high intensity image exceeding a threshold value TH1 from an average pixel value of a plurality of frames f.

FIG. 16 is a flowchart for removing a high intensity image that exceeds the threshold value TH1 from the average pixel value of frames f prior to and subsequent to a frame f.

At Step S90, the high intensity image determination unit 41 acquires a frame f that exceeds the threshold value TH1. The frame f that exceeds the threshold value TH1 corresponds to the frame f to which the unused flag is applied in the first embodiment.

At Step S91, the high intensity image determination unit 41 sets a frame number of an unused flag to the counter C.

At Step S92, the high intensity image determination unit 41 reads ultrasound images G of frames f(C−2) through f(C+2).

At Step S93, the high intensity image determination unit 41 calculates pixel values of the ultrasound images G of the frames f(C−2) through f(C+2) and calculates the average value AVE of the pixel values.

At Step S94, the high intensity image determination unit 41 sets a threshold value TH2 (refer to FIG. 14B) obtained by adding an incremental quality a to the average value AVE. The incremental quality a is set as a fixed value or a variable value.

At Step S95, the high intensity image determination unit 41 determines whether the respective pixel values of the frames f(C−2) through f(C+2) exceed the threshold value TH2. The high intensity image determination unit 41 moves to Step S96 with respect to each frame f that exceeds the threshold value TH2. The high intensity image determination unit 41 moves to Step S97 with respect to each frame f that does not exceed the threshold value TH2.

At Step S96, the high intensity image determination unit 41 applies an unused flag to the corresponding frame f that exceeds the threshold value TH2.

At Step S97, the high intensity image determination unit 41 determines whether an untreated frame f that exceeds the threshold value TH1 exists. When the untreated frame f is found to exist, the high intensity image determination unit 41 moves to Step S90. When the untreated frame f is found not to exist, the high intensity image determination unit 41 moves to Step S98.

At Step S98, the high intensity image determination unit 41 applies a used flag to a frame f with no unused flag applied thereto and stores it in the image memory.

Although the high intensity image determination unit 41 of the present modification has used the two frames prior to and subsequent to the frame f that exceeds the threshold value TH1, a frame f to be removed may be calculated based on three frames f using the previous two frames f.

According to the embodiments shown above, the high intensity image determination unit 41 is capable of removing a high intensity image having areas high in intensity partly and entirely upon acquisition of each ultrasound image G. Therefore, the time intensity curve arithmetic unit 42 is capable of obtaining a smooth time intensity curve in a ROI by taking a method such as interpolation.

The first through third embodiments and their modifications respectively have explained the embodiments in which the image data or sound ray data corresponding to one frame determined to be the high intensity image have been removed. It is however unnecessary to remove all of the image data or sound ray data corresponding to one frame. The ROI setting unit 45 may eliminate image data or sound ray data related to only a region of interest set to an ultrasound image G. The time intensity curve arithmetic unit 42 may interpolate pixel values of adjacent regions of interest with respect to a region of interest in which no pixel value exists, to thereby calculate a time intensity curve.

Many widely different embodiments may be configured without departing from the spirit and the scope of the present invention. It should be understood that the present invention is not limited to the specific exemplary embodiments described in the specification, except as defined in the appended claims.

What is claimed is:

1. An ultrasound diagnostic apparatus comprising:
   an image data generation unit configured to generate image data corresponding to one frame of a tomographic plane of a subject, based on sound ray data acquired by transmitting ultrasound to the subject to which an ultrasound contrast agent is administrated;
   a high intensity image determination unit configured to compare a strength of sound ray data corresponding to the one frame with a predetermined value and thereby determine whether the one frame is a high intensity image;
   a setting unit configured to set a region of interest onto an image based on the image data generated by the image data generation unit; and
   a time intensity curve arithmetic unit configured to perform an arithmetic operation on a time intensity curve which indicates changes in pixel values of the region of interest based on the image data for each of a plurality of frames, wherein image data of the region of interest in a frame that is determined to be the high intensity image is eliminated from the time intensity curve.

2. The ultrasound diagnostic apparatus according to claim 1, wherein the time intensity curve arithmetic unit is configured to eliminate the sound ray data corresponding to the one frame determined to be of the high intensity image and perform an interpolation operation on the pixel value of the eliminated sound ray data, based on a pixel value of a frame prior to or subsequent to the one frame.

3. An ultrasound diagnostic apparatus comprising:
   an image data generation unit configured to generate image data corresponding to one frame of a tomographic plane of a subject, based on sound ray data acquired by transmitting ultrasound to the subject to which an ultrasound contrast agent is administrated;
   a high intensity image determination unit configured to compare a pixel value of the image data with a predetermined value and thereby determine whether the one frame is a high intensity image;
   a setting unit configured to set a region of interest onto an image based on the image data generated by the image data generation unit; and
   a time intensity curve arithmetic unit configured to perform an arithmetic operation on a time intensity curve which indicates changes in pixel values of the region of interest set in the image based on the image data in each of a plurality of frames, wherein image data of the region of interest in a frame that is determined to be the high intensity image is eliminated from the time intensity curve.

4. The ultrasound diagnostic apparatus according to claim 3, wherein when the average of the pixel values is greater than or equal to the predetermined value within the image data corresponding to the one frame at a screen corresponding to one frame, the high intensity image determination unit is configured to determine the image of the one frame to be a high intensity image.

5. The ultrasound diagnostic apparatus according to claim 4, wherein the high intensity image determination unit is configured to segment the image data corresponding to the one frame into a plurality of areas and determine the image corresponding to the one frame to be a high intensity image when of the segmented areas, the areas in each of which the pixel value is greater than or equal to the predetermined value, exist in plural form.

6. The ultrasound diagnostic apparatus according to claim 5, wherein when the pixel value is greater than or equal to the predetermined value in a plurality of areas including the region of interest, the image corresponding to the one frame is determined to be a high intensity image.

7. The ultrasound diagnostic apparatus according to claim 3, wherein when the pixel value of each of image data corresponding to a sequence of plural frames is greater than or equal to the predetermined value, the high intensity image determination unit is configured to determine each of images corresponding to the frames to be a high intensity image.

8. The ultrasound diagnostic apparatus according to claim 7, wherein the predetermined value is calculated from the entire average pixel value corresponding to a sequence of few frames.

9. The ultrasound diagnostic apparatus according to claim 3, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

10. The ultrasound diagnostic apparatus according to claim 4, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

11. The ultrasound diagnostic apparatus according to claim 5, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

12. The ultrasound diagnostic apparatus according to claim 6, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

13. The ultrasound diagnostic apparatus according to claim 7, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

14. The ultrasound diagnostic apparatus according to claim 8, wherein the time intensity curve arithmetic unit is configured to eliminate image data corresponding to one frame determined to be the high intensity image and perform an interpolation operation on the pixel value of the eliminated image data, based on the pixel value of a frame prior to or subsequent to the one frame.

15. The ultrasound diagnostic apparatus according to claim 1, wherein the time intensity curve arithmetic unit is configured to perform an arithmetic operation on one of the average pixel value of the region of interest and the maximum pixel value of the region of interest.

16. The ultrasound diagnostic apparatus according to claim 2, wherein the time intensity curve arithmetic unit is configured to perform an arithmetic operation on one of the average pixel value of the region of interest and the maximum pixel value of the region of interest.

17. The ultrasound diagnostic apparatus according to claim 3, wherein the time intensity curve arithmetic unit is configured to perform an arithmetic operation on one of the average pixel value of the region of interest and the maximum pixel value of the region of interest.

18. The ultrasound diagnostic apparatus according to claim 4, wherein the time intensity curve arithmetic unit is configured to perform an arithmetic operation on one of the average pixel value of the region of interest and the maximum pixel value of the region of interest.

19. The ultrasound diagnostic apparatus according to claim 5, wherein the time intensity curve arithmetic unit is configured to perform an arithmetic operation on one of the average pixel value of the region of interest and the maximum pixel value of the region of interest.

20. A method of determining a time intensity curve, comprising:
   administering an ultrasound contrast agent to a subject;
   acquiring sound ray data by transmitting ultrasound to the subject;
   generating image data corresponding to one frame of a tomographic plane of the subject, based on the sound ray data;
   comparing a pixel value of the image data with a predetermined value;
   determining whether the one frame is a high intensity image;
   setting a region of interest onto an image based on the image data;
   performing an arithmetic operation on a time intensity curve which indicates changes in pixel values of the region of interest based on the image data for each of a plurality of frames, wherein image data of the region of interest in a frame that is determined to be the high intensity image is eliminated from the time intensity curve; and
   displaying the time intensity curve.

* * * * *